United States Patent
Takahashi

(10) Patent No.: US 12,279,903 B2
(45) Date of Patent: Apr. 22, 2025

(54) RADIATION IMAGE PROCESSING DEVICE AND RADIATION IMAGE PROCESSING METHOD

(71) Applicant: FUJIFILM Corporation, Tokyo (JP)

(72) Inventor: Tomoyuki Takahashi, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 620 days.

(21) Appl. No.: 17/534,825

(22) Filed: Nov. 24, 2021

(65) Prior Publication Data

US 2022/0079543 A1    Mar. 17, 2022

Related U.S. Application Data

(63) Continuation of application No. PCT/JP2020/020848, filed on May 27, 2020.

(30) Foreign Application Priority Data

May 27, 2019 (JP) .................................. 2019-098660
May 26, 2020 (JP) .................................. 2020-091087

(51) Int. Cl.
　　*G06T 5/00* (2024.01)
　　*A61B 6/00* (2006.01)
　　*A61B 6/42* (2024.01)

(52) U.S. Cl.
　　CPC .......... *A61B 6/5282* (2013.01); *A61B 6/4291* (2013.01)

(58) Field of Classification Search
　　CPC ..... A61B 6/032; A61B 6/5235; A61B 6/5211; A61B 6/4291; A61B 6/483; A61B 6/5294;
(Continued)

(56) References Cited

U.S. PATENT DOCUMENTS

2015/0063526 A1    3/2015 Kobayashi et al.
2016/0140720 A1*   5/2016 Naito ................... A61B 6/5211
　　　　　　　　　　　　　　　　　　　　　　　　　　　　　　　　 382/132
(Continued)

FOREIGN PATENT DOCUMENTS

JP    2014-207958 A    11/2014
JP    2015-043959 A    3/2015
(Continued)

OTHER PUBLICATIONS

International Search Report dated Aug. 25, 2020 in International Application No. PCT/JP2020/020848.
(Continued)

*Primary Examiner* — Quan M Hua
(74) *Attorney, Agent, or Firm* — Sughrue Mion, PLLC

(57) ABSTRACT

A radiation image processing device includes: a first estimation section that estimates components of radiation Ra having passed through a subject Obj using a first radiation image taken from the subject Obj; a second estimation section that estimates components of the radiation Ra, which have passed through an additional scattering element EL, using an estimation result of the first estimation section and scattering characteristics f2(X) of the additional scattering element EL; and a first image generation section that generates a second radiation image, which has been transmitted through the subject Obj and the additional scattering element EL, using an estimation result of the second estimation section.

18 Claims, 12 Drawing Sheets

(58) Field of Classification Search
CPC ....... A61B 6/4085; A61B 6/482; A61B 6/461; A61B 6/4233; A61B 6/4035; G06T 2207/10116; G06T 7/0012; G06T 2207/20016; G06T 11/005; G06T 2207/30004; G06T 5/70; G06T 5/50; G06T 5/10; G06T 2207/10124; G06T 7/60; G06T 7/62; G01T 1/00; G01T 1/2002; G01T 1/2006; G01T 1/2985; G01T 7/00; G01T 1/1648; G01T 1/20; G01T 1/2018; G01T 1/20188; G01T 1/202; G01T 1/24
See application file for complete search history.

(56) References Cited

U.S. PATENT DOCUMENTS

2016/0302752 A1* 10/2016 Ito .............................. G06T 5/40
2017/0055933 A1* 3/2017 Kawamura ........... G06T 11/005
2017/0221207 A1 8/2017 Imai
2017/0360391 A1* 12/2017 Kawamura ............ A61B 6/542

FOREIGN PATENT DOCUMENTS

| JP | 2015-051081 A | 3/2015 |
| JP | 2015-126864 A | 7/2015 |
| JP | 2016-172098 A | 9/2016 |
| JP | 2017-225525 A | 12/2017 |

OTHER PUBLICATIONS

Written Opinion of the International Searching Authority dated Aug. 25, 2020 in International Application No. PCT/JP2020/020848.
International Preliminary Report on Patentability dated Nov. 16, 2021 in International Application No. PCT/JP2020/020848.
Communication dated Oct. 4, 2022, issued in Japanese Application No. 2021-522800.

* cited by examiner

RADIATION IMAGE PROCESSING DEVICE AND RADIATION IMAGE PROCESSING METHOD

CROSS-REFERENCE TO RELATED APPLICATIONS

This application is a Continuation of PCT International Application No. PCT/JP2020/020848 filed on 27 May 2020, which claims priority under 35 U.S.C. § 119(a) to Japanese Patent Applications No. 2019-098660 filed on 27 May 2019 and No. 2020-091087 filed on 26 May 2020. The above application is hereby expressly incorporated by reference, in its entirety, into the present application.

BACKGROUND OF THE INVENTION

1. Field of the Invention

The present invention relates to a radiation image processing device and a radiation image processing method that perform image processing on a radiation image.

2. Description of the Related Art

A radiography device imaging a subject using radiation, such as an X-ray, has been spread in the past. For example, in a case where a subject is a human or an animal, radiation images are used for the diagnosis or the like of a lesion.

It is desirable that a radiation image is formed in radiography using only primary radiation directly transmitted through a subject and the like. However, in a case where radiation is incident on elements of the radiography device and/or a subject and the like, a part of the radiation is scattered and forms so-called scattered radiation. Components (hereinafter, referred to as scattered radiation components) generated in a radiation image due to scattered radiation are noise. For this reason, a grid absorbing scattered radiation components is usually used at the time of imaging, and/or scattered radiation components are reduced by image processing performed after imaging.

There is image processing that is called, for example, virtual grid as the image processing for reducing scattered radiation components after imaging (JP2014-207958A (corresponding to US2017/221207A1) and JP2016-172098A). Virtual grid is image processing for obtaining a radiation image from which scattered radiation components have been reduced by estimating the quantity of scattered radiation components included in each pixel of the radiation image using the body thickness of a subject and subtracting the estimated quantity of scattered radiation components from an original radiation image.

SUMMARY OF THE INVENTION

Image processing for reducing scattered radiation components included in a radiation image has been known. However, in recent years, there has been a demand for a technique for estimating scattered radiation components with higher accuracy and reducing the scattered radiation components. The reason for this is to more accurately make a diagnosis and the like using a radiation image.

Further, in recent years, not only radiation images taken for diagnosis and the like have been displayed but also a calculation and the like have been made using radiation images to provide a radiation image in which some tissues and the like included in a subject are highlighted or information about the composition and the like of the subject. For example, radiation images used for diagnosis and the like are not limited to so-called projection images, and a soft part image where soft part tissues of a subject are extracted (or highlighted) and/or a bony part image where bony parts of a subject are extracted may be used. The soft part image and/or the bony part image are generated by so-called subtraction processing. The subtraction processing is processing for giving predetermined weight to two types of radiation images, which are different from each other in energies and the like of radiation used for imaging, and calculating a difference between the radiation images; and is processing using an attenuation coefficient for radiation that varies according to composition. Further, a bone mineral content (bone density) may be measured by calculation using, for example, the pixel values of a radiation image.

In a case where a radiation image is used for calculation as described above, scattered radiation components are required to be particularly accurately reduced from the radiation image used for calculation. The reason for this is that errors caused by scattered radiation components negatively affect calculation results and it is difficult to obtain accurate calculation results in a case where a calculation using a radiation image is made.

An object of the invention is to provide a radiation image processing device and a radiation image processing method that can acquire a radiation image from which scattered radiation components are accurately removed in consideration of an element interposed between a subject and a radiation detector.

A radiation image processing device according to an aspect of the invention comprises a processor. The processor acquires a first radiation image that is taken from a subject using radiation; estimates a component of the radiation, which has passed through the subject, using the first radiation image; estimates a component of the radiation, which has passed through an element through which the radiation further passes after passing through the subject, using an estimation result of the component of the radiation transmitted through the subject and scattering characteristics of the element; and generates a second radiation image, in which an image of the subject is formed by the radiation transmitted through the subject and the element, using an estimation result of the component of the radiation transmitted through the element.

It is preferable that the processor estimates the component of the radiation transmitted through the subject and a component of the radiation scattered by the subject. It is preferable that the processor estimates a body thickness of the subject using the first radiation image and estimates a component of the radiation having passed through the subject using the estimated body thickness of the subject. It is preferable that the processor estimates the component of the radiation transmitted through the subject and a component of the radiation scattered by the subject on the basis of the estimated body thickness of the subject.

It is preferable that the estimation result of the component of the radiation transmitted through the subject is an intensity distribution of the radiation having passed through the subject and the intensity distribution of the radiation having passed through the subject includes the component of the radiation transmitted through the subject and a component of the radiation scattered by the subject. It is preferable that the processor estimates the component of the radiation transmitted through the subject and the element or a component of the radiation scattered by at least one of the subject or the element. It is preferable that the processor estimates a component of the radiation, which has passed through the element, by causing the scattering characteristics of the element to act on the estimation result of the component of the radiation transmitted through the subject.

It is preferable that the scattering characteristics determine a distribution of an amount of radiation to be transmitted through the element and/or an amount of radiation to be scattered by the element. It is preferable that the scattering characteristics include a first characteristic determining the distribution of the amount of radiation to be transmitted through the element and a second characteristic determining the distribution of the amount of radiation to be scattered by the element.

It is preferable that, in a case where the processor estimates the component of the radiation transmitted through the subject and the element, the processor generates the second radiation image by making an image of the estimation result of the component of the radiation transmitted through the element. It is preferable that, in a case where the processor estimates a component of the radiation scattered by the subject or the element, the processor generates the second radiation image by subtracting the estimation result of the component of the radiation, which has been transmitted through the element, from the first radiation image.

A radiation image processing device according to another aspect of the invention comprises a processor. The processor is configured to detect radiation transmitted through a subject by a radiation detector in a state where an element is interposed between the subject and the radiation detector, to acquire an imaging condition at a time of acquisition of a radiation image of the subject, to derive a body thickness distribution of the subject on the basis of the radiation image and the imaging condition, to acquire radiation characteristics of the element corresponding to the body thickness distribution, to derive a primary radiation distribution and a scattered radiation distribution of the radiation, which is detected by the radiation detector, using the imaging condition, the body thickness distribution, and the radiation characteristics of the element, to calculate an error between a sum of the primary radiation distribution and the scattered radiation distribution and a pixel value at each position in the radiation image, to update the body thickness distribution so that the error is less than a predetermined threshold value, and to repeat the derivation of the radiation characteristics and the derivation of the primary radiation distribution and the scattered radiation distribution based on the updated body thickness distribution.

It is preferable that the processor is configured to output a processed radiation image that has the primary radiation distribution derived on the basis of the body thickness distribution of the subject where the error is less than the threshold value as pixel values. It is preferable that a first table showing a relationship between the body thickness distribution and scattered radiation transmittance of the element interposed between the subject and the radiation detector, or a second table showing a relationship between the body thickness distribution and primary radiation transmittance of the element interposed between the subject and the radiation detector is stored in a storage, and the processor acquires the primary radiation transmittance or the scattered radiation transmittance, which is radiation characteristics of the element corresponding to the body thickness distribution, with reference to the first and second tables according to the imaging condition. It is preferable that the element is at least one of an imaging table on which the subject is to be placed, a top board, a grid, or an air layer.

A radiation image processing method executed by a processor according to another aspect of the invention comprises: a step of acquiring a first radiation image that is taken from a subject using radiation; a step of estimating a component of the radiation, which has passed through the subject, using the first radiation image; a step of estimating a component of the radiation, which has passed through an element through which the radiation further passes after passing through the subject, using an estimation result of the component of the radiation having passed through the subject and scattering characteristics of the element; and a step of generating a second radiation image, in which an image of the subject is formed by the radiation transmitted through the subject and the element, using an estimation result of the component of the radiation having passed through the element.

A radiation image processing method executed by a processor according to another aspect of the invention comprises: a step of acquiring an imaging condition at a time of acquisition of a radiation image of a subject by detecting radiation transmitted through the subject by a radiation detector in a state where an element is interposed between the subject and the radiation detector; a step of deriving a body thickness distribution of the subject on the basis of the radiation image and the imaging condition; a step of acquiring radiation characteristics of the element corresponding to the body thickness distribution; a step of deriving a primary radiation distribution and a scattered radiation distribution of the radiation, which is detected by the radiation detector, using the imaging condition, the body thickness distribution, and the radiation characteristics of the element; and a step of calculating an error between a sum of the primary radiation distribution and the scattered radiation distribution and a pixel value at each position in the radiation image, updating the body thickness distribution so that the error is less than a predetermined threshold value, and repeating the derivation of the radiation characteristics and the derivation of the primary radiation distribution and the scattered radiation distribution based on the updated body thickness distribution.

According to the radiation image processing device and the radiation image processing method of the aspects of the invention, it is possible to acquire a radiation image from which scattered radiation components are accurately removed in consideration of an element interposed between a subject and a radiation detector.

DESCRIPTION OF THE PREFERRED EMBODIMENTS

First Embodiment

Figure 1:
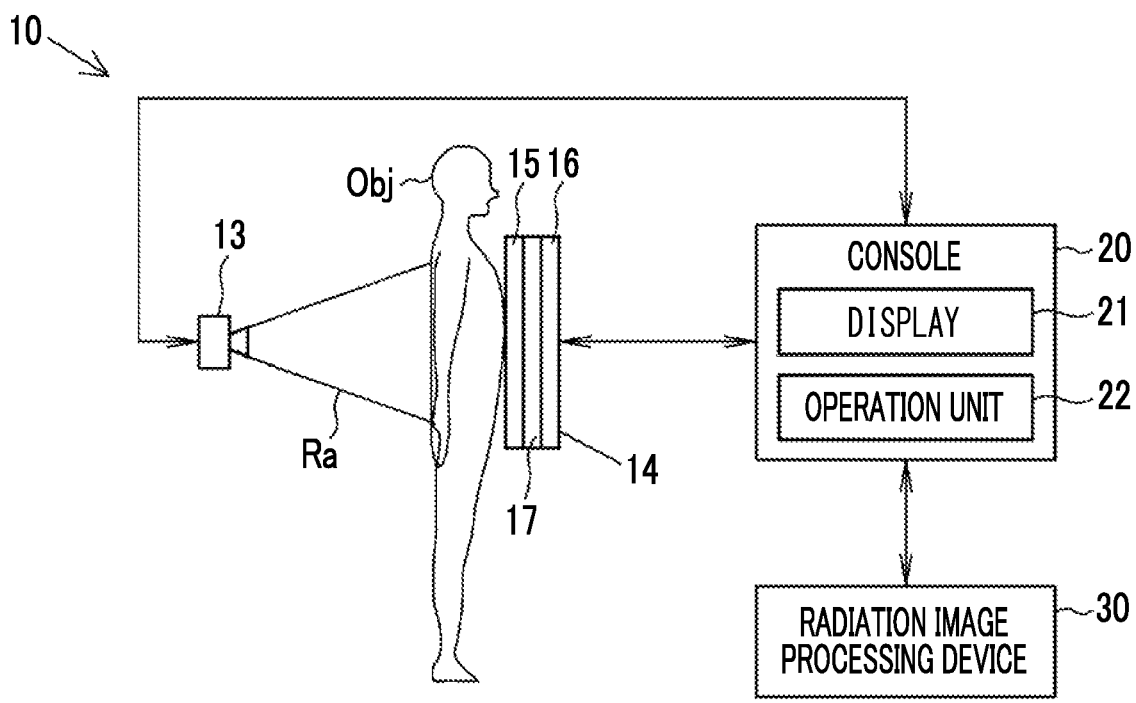
FIG. 1 is a diagram illustrating the configuration of a radiography system.

As shown in FIG. 1, a radiography system 10 comprises a radiation source 13, a radiography panel 14, a console 20, and a radiation image processing device 30.

Figure 2:
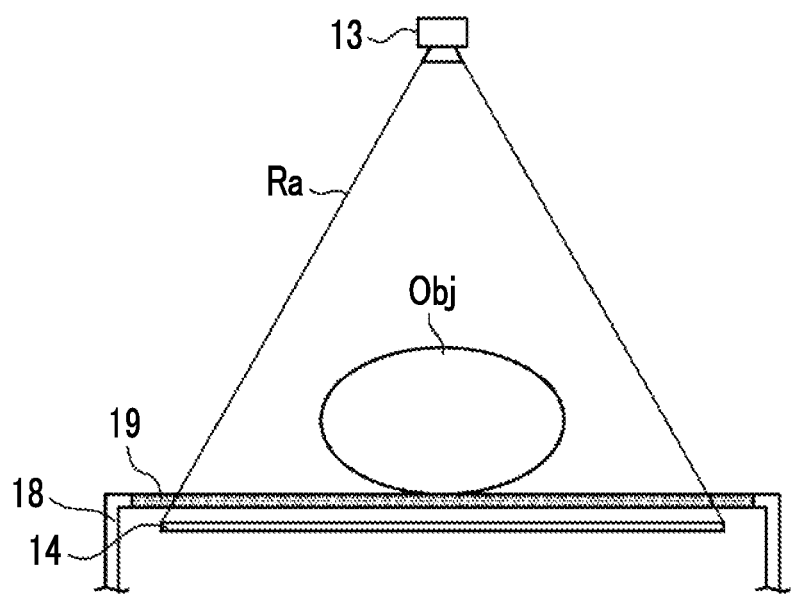
FIG. 2 is a diagram illustrating elements that are provided between a subject and a radiography panel.

The radiography system 10 irradiates a radiography panel 14 with radiation, which is emitted from a radiation source 13, such as an X-ray source, and has been transmitted through a subject Obj, to acquire a radiation image of the subject Obj lying on an imaging table 18 (see FIG. 2). Accordingly, the range of radiation to be applied to the subject Obj is defined. The radiation image is input to the console 20.

The radiation source 13, the radiography panel 14, and the console 20 form a radiography device. The radiation source 13 is a device generating radiation Ra required for imaging, and consists of a radiation tube that generates the radiation Ra, a high voltage generating circuit that generates a high voltage required to allow the radiation tube to generate the radiation Ra, and the like. The radiation source 13 can generate a plurality of types of radiations having different qualities (energy distributions (hereinafter, simply referred to as energies) with respect to wavelengths) by adjusting the tube voltage, the tube current and the like of the radiation tube. The energy of the radiation generated by the radiation source 13 is one of imaging conditions. In this embodiment, the radiation source 13 is an X-ray source generating an X-ray. For this reason, the radiography system 10 is an X-ray imaging system that acquires the X-ray image of a subject Obj by imaging the subject Obj using an X-ray. The subject Obj is, for example, a human.

The radiography panel 14 is a radiation detector that images the subject Obj using the radiation Ra generated by the radiation source 13. The radiography panel 14 is a so-called flat panel detector (FPD), and outputs the radiation image of the subject Obj by detecting the radiation Ra, which is transmitted through the subject Obj, and converting the radiation Ra into electrical signals. It is preferable that the radiography panel 14 is portable. For example, the radiography panel 14 is detachably mounted on the imaging table 18 together with a grid to be described below by a mounting portion that is provided on the lower surface of the imaging table 18 (see FIG. 2). The radiography panel 14 may be fixed to the imaging table 18.

In the imaging using the radiography panel 14, the grid (not shown) can be used together as necessary. The grid is a device for removing scattered radiation components of radiation, and is, for example, a stationary Lysholm grid, a movable Bucky's grid, or the like. The grid has configuration where lead or the like through which radiation is not transmitted and interspace materials, such as aluminum or fibers, through which radiation is easily transmitted are alternately arranged at a fine grid density of, for example, about 4.0 pieces/mm In a case where the grid is used, the scattered radiation components of radiation transmitted through the subject Obj can be removed but cannot be completely removed. For this reason, not only primary radiation components of radiation transmitted through the subject Obj but also the scattered radiation components are included in the radiation image acquired by the radiography panel 14.

In this embodiment, the radiography panel 14 comprises two radiation detectors, that is, a first radiation detector 15 and a second radiation detector 16. One detector, which is disposed to be closer to the subject Obj and the radiation source 13, of the first and second radiation detectors 15 and 16 is the first radiation detector 15, and the other detector thereof, which is disposed to be farther from the subject Obj and the radiation source 13, is the second radiation detector 16. The first and second radiation detectors 15 and 16 detect the radiation Ra, which is transmitted through the subject Obj, for each pixel. Further, each of the first and second radiation detectors 15 and 16 outputs the radiation image of the subject Obj.

However, the radiography panel 14 comprises a radiation energy conversion filter 17 between the first and second radiation detectors 15 and 16. The radiation energy conversion filter 17 is, for example, a copper plate or the like, and absorbs the low-energy components of the radiation Ra. For this reason, the energy of the radiation Ra is changed until the radiation Ra reaches the second radiation detector 16 after being transmitted through the first radiation detector 15. Accordingly, the radiography panel 14 simultaneously images the specific subject Obj under the same imaging condition (with the same radiation Ra), but a radiation image G1 output from the first radiation detector 15 and a radiation image G2 output from the second radiation detector 16 are radiation images that are taken using radiation Ra having energies substantially different from each other.

It is preferable that the first radiation detector 15 or the second radiation detector 16 can repeatedly record and read out a radiation image. Each of the first and second radiation detectors 15 and 16 is any one of an indirect conversion type detector or a direct conversion type detector, or different types of detectors may be employed as the first and second radiation detectors 15 and 16. The indirect conversion type detector is a detector that converts the radiation Ra into visible light using a scintillator consisting of cesium iodide (CsI) or the like and photoelectrically converts the visible light to indirectly obtain electrical signals. The direct conversion type detector is a detector that directly converts the radiation Ra into electrical signals using a scintillator consisting of amorphous selenium or the like. Further, each of the first and second radiation detectors 15 and 16 may be a penetration side sampling (PSS) detector or may be an irradiation side sampling (ISS) detector. A PSS system is a system in which a scintillator is disposed on a side, which faces the subject Obj, of a thin film transistor (TFT) that reads out electrical signals. An ISS system is a system in which a TFT and a scintillator are arranged in this order from the subject Obj on the contrary to the PSS system.

The console 20 is a control device (computer) for controlling the operations of the radiation source 13 and the radiography panel 14, and comprises a display 21, an operation unit 22, and the like. The display 21 is, for example, a liquid crystal display or the like, and displays necessary items according to operations, settings, or the like in addition to taken radiation images. The operation unit 22 is, for example, a keyboard and/or a pointing device, or the like that are used for the setting input of imaging conditions and the like and the operations of the radiation source 13 and the radiography panel 14. Each of the display 21 and the operation unit 22 can be formed of a touch panel.

The radiation image processing device 30 performs image processing using radiation images, which are taken from the subject Obj, for display in a diagnosis and the like or for detailed image analysis according to a diagnosis and the like. The radiation image processing device 30 is directly connected to the console 20, and can acquire the radiation images, which are taken from the subject Obj, in real time and use the radiation images in image processing. Further, the radiation image processing device 30 can indirectly acquire radiation images through radiology information systems (RIS), hospital information systems (HIS), picture archiving and communication systems (PACS), a digital imaging and communications in medicine (DICOM) server included in PACS, or the like instead of being directly connected to the console 20 and use the radiation images in the image processing.

Furthermore, elements through which the radiation Ra further passes after passing through the subject Obj are provided between the subject Obj and the radiography panel 14. In an actual imaging aspect, for example, the subject Obj may be imaged in a state where the subject Obj is disposed on the imaging table 18 as shown in FIG. 2. In this case, a top board 19 of the imaging table 18 is the element through which the radiation Ra further passes after passing through the subject Obj. In addition, the grid that is used to reduce scattered radiation, a gel mat or a blanket that is spread between the subject Obj and the imaging table 18, an air gap (air layer) that is formed between the top board 19 and the radiography panel 14, and the like are the elements through which the radiation Ra further passes after passing through the subject Obj. Each of these elements is an additional device component for the convenience of imaging, and significantly absorbs and scatters radiation. Accordingly, in this embodiment, the above-mentioned respective elements are collectively referred to as an additional scattering element EL (see FIG. 4).

"Passing" with regard to the radiation Ra means that the radiation Ra passes through the subject Obj, the additional scattering element EL, or the like, and includes a case where the radiation Ra is transmitted through the subject Obj, the additional scattering element EL, or the like and a case where the radiation Ra passes in a direction different from the incident direction thereof due to the scattering of the subject Obj or the additional scattering element EL. "Transmission" with regard to the radiation Ra means that the radiation Ra passes through the subject Obj, the additional scattering element EL, or the like substantially in the incident direction thereof, and includes a case where the radiation Ra passes through the subject Obj, the additional scattering element EL, or the like substantially in the incident direction thereof in a state where some components of the radiation Ra are absorbed by the subject Obj, the additional scattering element EL, or the like. "Scattering" with regard to the radiation Ra means that the radiation Ra passes through the subject Obj, the additional scattering element EL, or the like in a direction different from the incident direction thereof.

Figure 3:
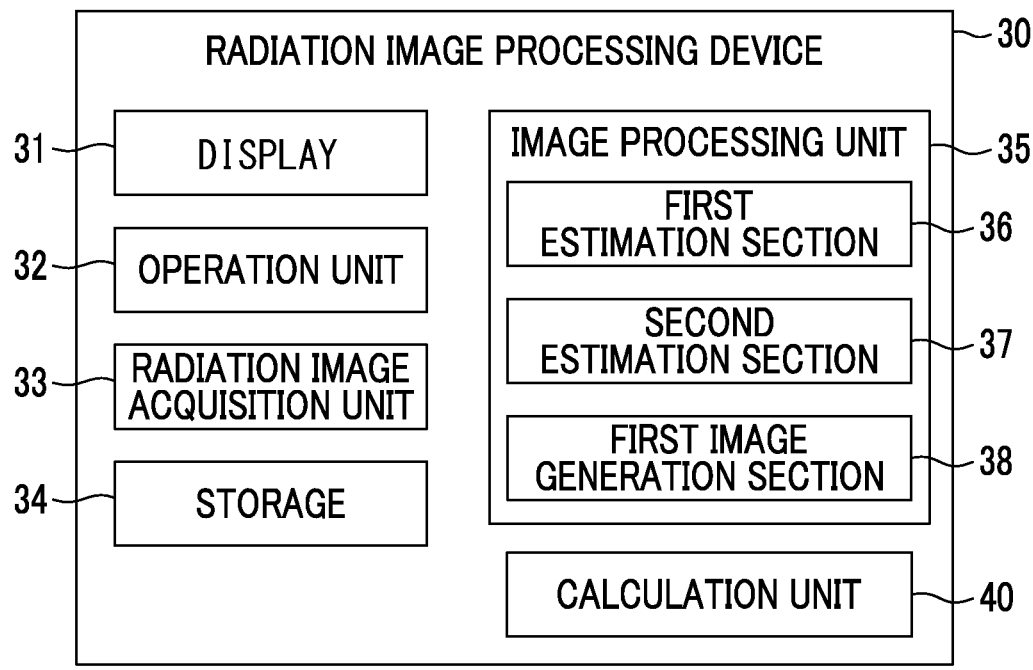
FIG. 3 is a block diagram showing the configuration of a radiation image processing device according to a first embodiment.

As shown in FIG. 3, the radiation image processing device 30 is a so-called computer and comprises a display 31, an operation unit 32, a radiation image acquisition unit 33, an image processing unit 35, and a calculation unit 40. In the radiation image processing device 30, programs related to various types of processing are incorporated in a program memory. The programs incorporated in the program memory are operated by a central controller (not shown) formed of a processor, so that the functions of the radiation image acquisition unit 33, the image processing unit 35, and the calculation unit are realized. Accordingly, the functions of a first estimation section 36, a second estimation section 37, and a first image generation section 38 included in the image processing unit 35 are realized.

The display 31 is a liquid crystal display or the like, and displays the taken radiation images, images generated by the radiation image processing device 30, and the like. The operation unit 32 is a keyboard and/or a pointing device, or the like that are used to operate the radiation image processing device 30. Each of the display 31 and the operation unit 32 can be formed of a touch panel. The radiation image processing device 30 is a device separate from the console 20 in this embodiment, but a part of the radiation image processing device 30 or the entire radiation image processing device 30 can be provided in the console 20. In this case, the display 21 and/or the operation unit 22 of the console 20 can be used as the display 31 and/or the operation unit 32 of the radiation image processing device 30. Further, the console 20 forms the radiation image processing device 30 in a case where the entire radiation image processing device 30 is provided in the console 20.

The radiation image acquisition unit 33 acquires radiation images that are taken from the subject Obj using the radiation Ra. The radiation image acquisition unit 33 can acquire radiation images from the console 20, RIS, HIS, PACS, or the like. In this embodiment, the radiation image acquisition unit 33 directly acquires the radiation images, which are taken by the radiography system 10, from the console 20. Further, the radiation image acquisition unit 33 acquires the radiation image G1 output from the first radiation detector 15 and the radiation image G2 output from the second radiation detector 16. In a case where the radiation image acquisition unit 33 acquires radiation images, the radiation image acquisition unit 33 may acquire not only so-called original images (images not subjected to image processing and the like) but also radiation images subjected to various types of processing, such as processing for adjusting contrast and the like or other image processing.

The image processing unit 35 generates radiation images. The radiation images generated by the image processing unit 35 are images in which an image of the subject is formed by the radiation Ra transmitted through the subject Obj and the additional scattering element EL. That is, the radiation images generated by the image processing unit 35 are scattered radiation component-reduced images in which components (scattered radiation components) of the radiation Ra scattered by the subject Obj and/or the additional scattering element EL are reduced from the taken radiation images (the radiation images acquired by the radiation image acquisition unit 33). For this purpose, the image processing unit 35 comprises the first estimation section 36, the second estimation section 37, and the first image generation section 38. In order to distinguish the taken radiation images from the radiation images generated by the image processing unit 35, the taken radiation images will be referred to as first radiation images 51 (see FIG. 5) and the radiation images generated by the image processing unit 35 will be referred to as second radiation images (not shown) in the following description.

Figure 4:
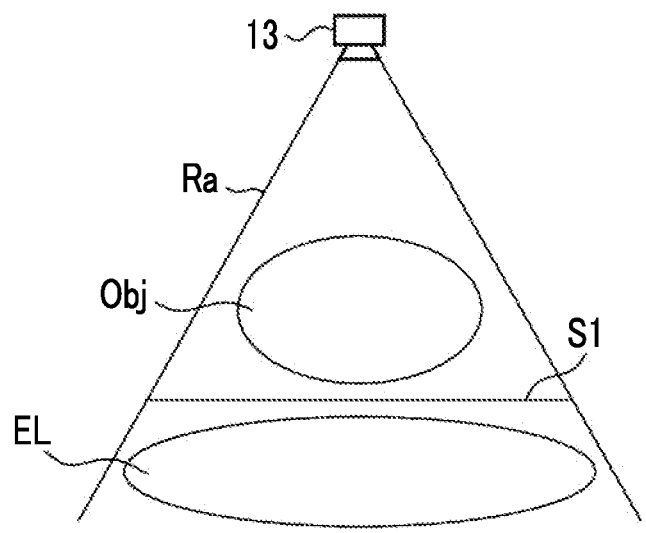
FIG. 4 is a diagram illustrating a position where components of radiation having passed through the subject are estimated.

The first estimation section 36 estimates the components of the radiation Ra having passed through the subject Obj using the first radiation images 51. "Radiation Ra having passed through the subject Obj" in estimation processing (hereinafter, referred to as first estimation processing) performed by the first estimation section 36 is radiation Ra that has passed through the subject Obj and does not yet pass through the additional scattering element EL, such as the top board 19, (not yet incident on the additional scattering element EL). That is, as shown in FIG. 4, the first estimation section 36 estimates the components of the radiation Ra obtained at a position S1 between the subject Obj and the additional scattering element EL.

Figure 5:
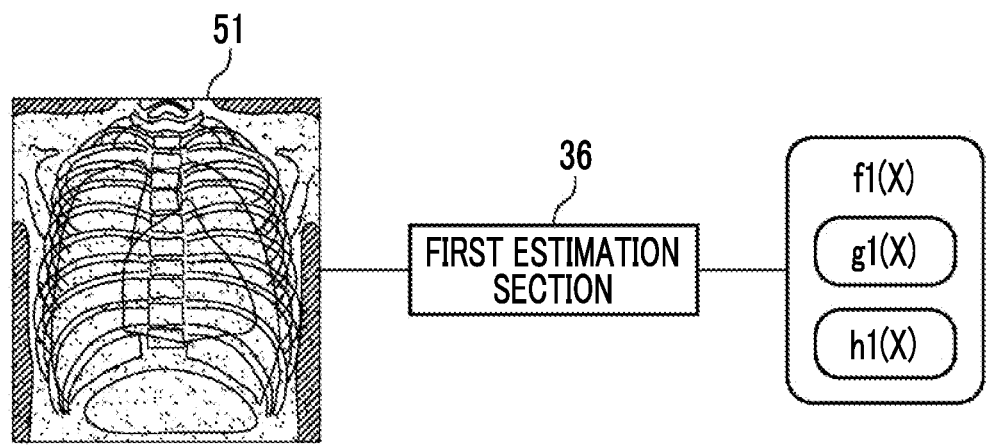
FIG. 5 is a diagram illustrating the functions of a first estimation section.

Further, the components of the radiation Ra having passed through the subject Obj mean the components of the radiation Ra transmitted through the subject Obj and/or the components of the radiation Ra scattered by the subject Obj. That is, the components of the radiation Ra transmitted through the subject Obj are so-called primary radiation components having passed through the subject Obj. The components of the radiation Ra scattered by the subject Obj are so-called scattered radiation components having passed through the subject Obj. In a case where the subject Obj is regarded as an operator g1 generating primary radiation components and an operator h1 generating scattered radiation components with regard to radiation Ra incident on the subject Obj toward an arbitrary position X, the primary radiation components having passed through the subject Obj are "g1(X)" and the scattered radiation components having passed through the subject Obj are "h1(X)" as shown in FIG. 5.

The first estimation section 36 can estimate the primary radiation components g1(X) having passed through the subject Obj, the scattered radiation components h1(X) having passed through the subject Obj, or both of these using the first radiation images 51. In this embodiment, the first estimation section 36 estimates each of the primary radiation components g1(X) having passed through the subject Obj and the scattered radiation components h1(X) having passed through the subject Obj using the first radiation images 51.

In a case where the first estimation section 36 estimates the primary radiation components g1(X), which have passed through the subject Obj, from the first radiation images 51, the first estimation section 36 can estimate the scattered radiation components h1(X), which have passed through the subject Obj, by subtracting the estimated primary radiation components g1(X) from the first radiation images 51. Further, in a case where the first estimation section 36 estimates the scattered radiation components h1(X), which have passed through the subject Obj, from the first radiation images 51, the first estimation section 36 can estimate the primary radiation components g1(X), which have passed through the subject Obj, by subtracting the estimated scattered radiation components h1(X) from the first radiation images 51.

For example, the body thickness of the subject Obj is estimated using the first radiation images 51 and the components of the radiation Ra having passed through the subject Obj are estimated using the estimated body thickness of the subject Obj, so that the first estimation processing performed by the first estimation section 36 can be performed. In this case, the first estimation section 36 estimates the primary radiation components g1(X) of the radiation Ra, which have been transmitted through the subject Obj, and the scattered radiation components h1(X) of the radiation Ra, which have been scattered by the subject Obj, for each pixel of the first radiation images 51 (or for each predetermined section consisting of a plurality of pixels) on the basis of the estimated body thickness of the subject Obj.

Figure 6:
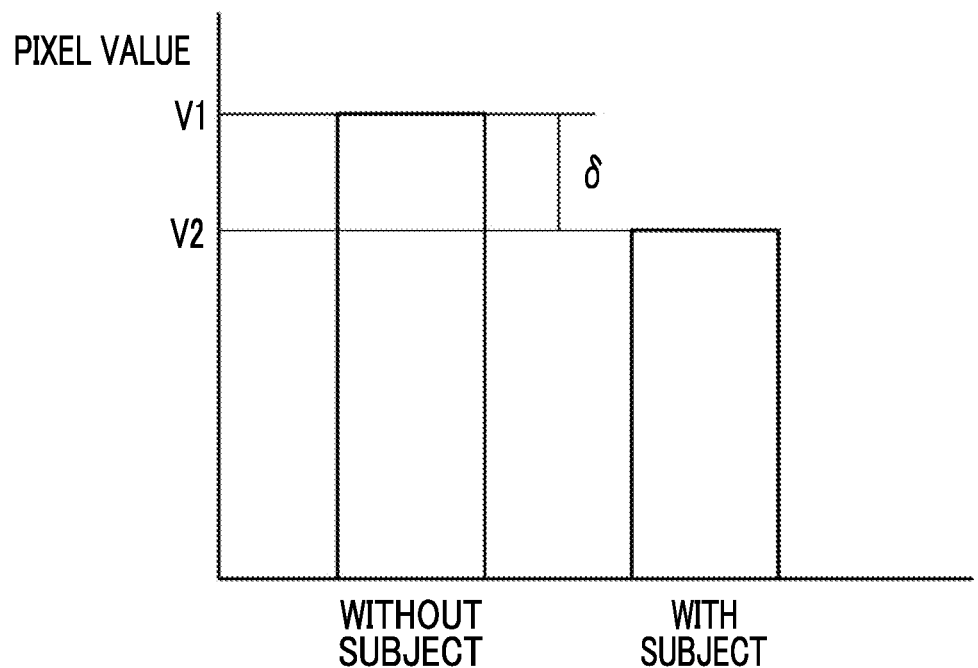
FIG. 6 is a diagram illustrating a method of estimating the body thickness of the subject.

For example, as shown in FIG. 6, a pixel value V2 in a case where a subject Obj is present ("with subject") is smaller than a pixel value V1 in a case where the subject Obj is not present ("without subject"). This is due to the absorption and the like of the subject Obj. For this reason, a difference δ (=V1−V2) between these pixel values is related to the body thickness of the subject Obj. Meanwhile, the pixel value V1 in a case where the subject Obj is not present can be known from the pixel value of a region (direct region) where the radiation Ra reaches the radiography panel 14 without passing through the subject Obj or an experiment (imaging in a state where the subject Obj is not placed) that is performed in advance. For this reason, the first estimation section 36 can estimate the body thickness of the subject Obj from the pixel value V2 of the first radiation images 51 that are taken in a state where the subject Obj is placed.

Further, both of the primary radiation components g1(X) and the scattered radiation components h1(X) having passed through the subject Obj are related to the body thickness of the subject Obj. For example, as the body thickness of the subject Obj is increased, the primary radiation components g1(X) are reduced due to the absorption and the like of the subject Obj and the scattered radiation components h1(X) are increased with respect to incident radiation Ra. The properties of the subject Obj, that is, the amount of radiation Ra, which has a specific energy, to be transmitted through the subject Obj and the amount of radiation Ra, which has a specific energy, to be scattered by the subject Obj can be obtained in advance from experiments and the like before radiography. For this reason, the first estimation section 36 has characteristics (hereinafter, referred to as subject scattering characteristics) related to the amount of transmitted radiation and the amount of scattered radiation for each subject Obj or for each portion to be imaged of the subject Obj in the format of a function, a conversion table, or the like. Then, the amount of transmitted radiation and the amount of scattered radiation are obtained using the energy and the like of radiation Ra used for imaging and the estimated body thickness of an actual subject Obj, so that the primary radiation components g1(X) and the scattered radiation components h1(X) having passed through the subject Obj are estimated.

Figure 7:
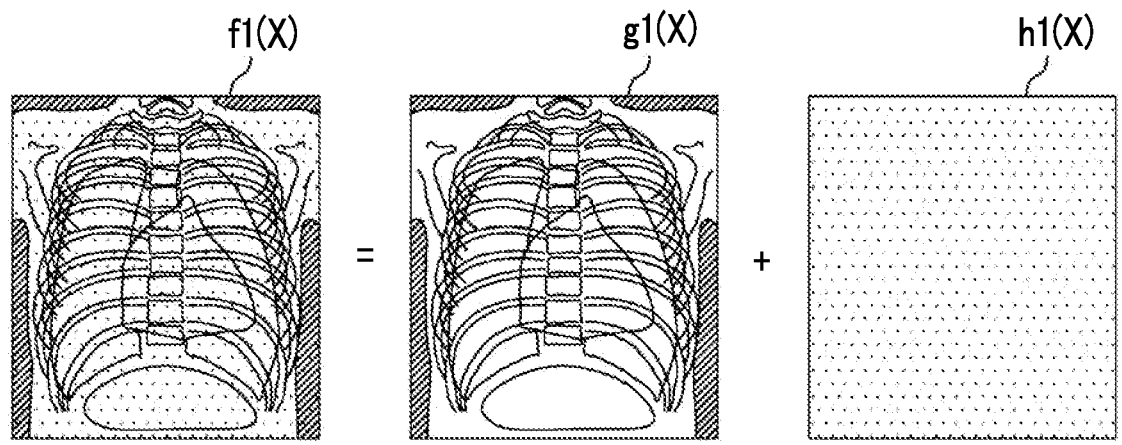
FIG. 7 is a diagram illustrating the estimation result of the first estimation section.

An estimation result (hereinafter, referred to as a first estimation result) output from the first estimation section 36 is the primary radiation components g1(X) obtained at the position S1 where the radiation has passed through the subject Obj, the scattered radiation components h1(X) obtained at the position S1 where the radiation has passed through the subject Obj, or an intensity distribution f1(X) of the radiation Ra obtained at the position S1 where the radiation has passed through the subject Obj. The intensity distribution f1(X) of the radiation Ra obtained at the position S1 is, for example, the sum or the weighted sum of the primary radiation components g1(X) and the scattered radiation components h1(X). In this embodiment, as shown in FIG. 7, the first estimation section 36 outputs the intensity distribution f1(X) of the radiation Ra obtained at the position S1 where the radiation has passed through the subject Obj as the first estimation result, for example, in the format of an image or the format of a database that can construct an image. The first estimation section 36 also can output one of the primary radiation components g1(X) or the scattered radiation components h1(X) having passed through the subject Obj as an estimation result.

The second estimation section 37 estimates the components of the radiation Ra having passed through the additional scattering element EL using the estimation result of the first estimation section 36 and the scattering characteristics of the additional scattering element EL through which the radiation Ra further passes after passing through the subject. "Having passed through the additional scattering element EL" in estimation processing (hereinafter, referred to as second estimation processing) performed by the second estimation section 37 means that the radiation passes through a position where the subject Obj is present and then passes through the additional scattering element EL. For this reason, "having passed through the additional scattering element EL" in the second estimation processing includes a case where the radiation directly passes through the additional scattering element EL without being transmitted through the subject Obj due to the specific shape and the like of the subject Obj.

More specifically, the second estimation section 37 estimates the components of the radiation Ra that have been transmitted through the subject Obj and the additional scattering element EL or the components of the radiation Ra that have been scattered by at least one of the subject Obj or the additional scattering element EL. The components of the radiation Ra that have been transmitted through the subject Obj and the additional scattering element EL are so-called primary radiation components having passed through the additional scattering element EL. The components of the radiation Ra that have been scattered by at least one of the subject Obj or the additional scattering element EL are so-called scattered radiation components having passed through the additional scattering element EL.

The scattering characteristics of the additional scattering element EL determine the distribution of the amount of radiation to be transmitted through the additional scattering element EL and/or the amount of radiation to be scattered by the additional scattering element EL. In this embodiment, the scattering characteristics of the additional scattering element EL are scattering characteristics f2(X) including a first characteristic g2(X) determining the distribution of the amount of radiation to be transmitted through the additional scattering element EL and a second characteristic h2(X) determining the distribution of the amount of radiation to be scattered by the additional scattering element EL. Specifically, the scattering characteristics f2(X) are the sum or the weighted sum of the first characteristic g2(X) and the second characteristic h2(X) and, for example, "f2(X)=g2(X)+h2(X)" is satisfied.

The first characteristic g2(X) is a function, a conversion table, or the like that determines the transmission dose of the radiation Ra to be directly incident on the additional scattering element EL toward an arbitrary position X without passing through the subject Obj. Further, the second characteristic h2(X) is a function, a conversion table, or the like that determines the transmission dose of the radiation Ra to be directly incident on the additional scattering element EL toward an arbitrary position X without passing through the subject Obj. For example, in a case where the additional scattering element EL is only the top board 19 of the imaging table 18, the first characteristic g2(X) determines the distribution of the transmission dose of the top board 19 and the second characteristic h2(X) determines the distribution of the amount of radiation to be scattered by the top board 19. The state of the specific configuration of the additional scattering element EL (the use, non-use, or the like of the imaging table 18 or the like) is already known before radiography. For this reason, the first characteristic g2(X) and the second characteristic h2(X) can be obtained in advance from experiments and the like before radiography for, for example, each specific configuration of the additional scattering element EL or for each combination of the additional scattering element EL. Further, in a case where the additional scattering element EL is regarded as an element generating primary radiation components and scattered radiation components from incident radiation, the first characteristic g2(X) is an operator generating the primary radiation components corresponding to the incident radiation and the second characteristic h2(X) is an operator generating the scattered radiation components corresponding to the incident radiation.

In this embodiment, the second estimation section 37 has the first characteristic g2(X) and the second characteristic h2(X) in advance for, for example, each specific configuration of the additional scattering element EL. As a result, the second estimation section 37 has the scattering characteristics f2(X) of the additional scattering element EL in advance. However, the second estimation section 37 can acquire the first characteristic g2(X), the second characteristic h2(X), and/or the scattering characteristics f2(X) as necessary.

Figure 8:
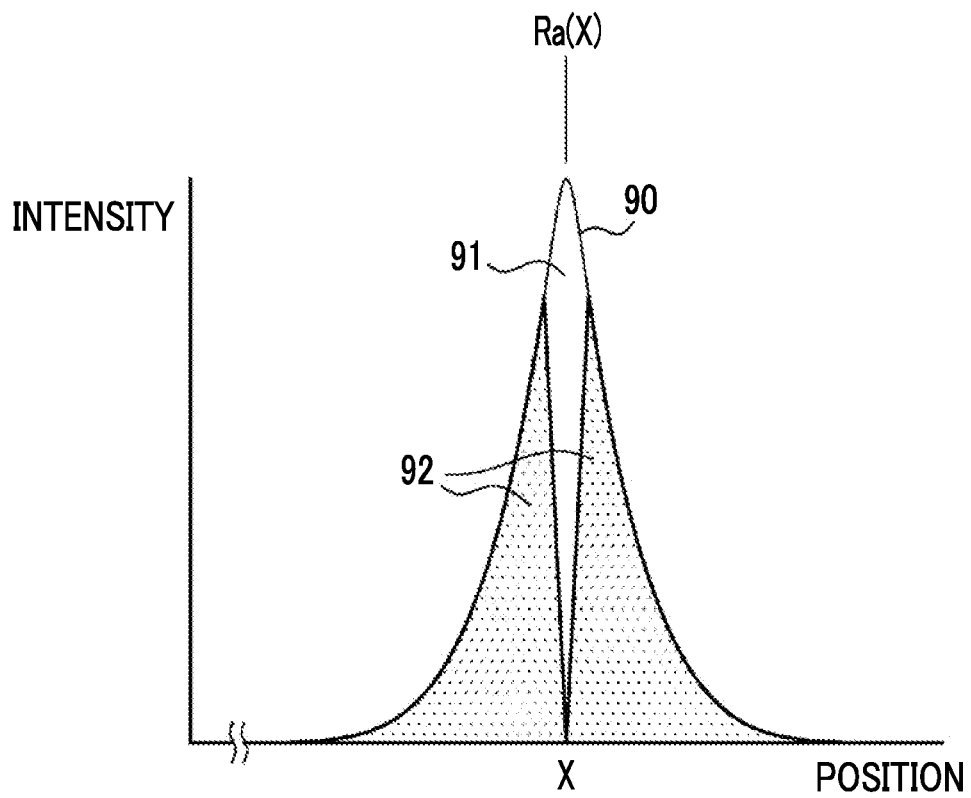
FIG. 8 is a graph showing a point spread function.

As shown in FIG. 8, the intensity distribution of radiation Ra(X), which is incident toward an arbitrary point X and has passed through the additional scattering element EL, can be approximated by a point spread function (PSF) 90. The PSF 90 is, for example, Gaussian. Further, components, which reach the arbitrary point X and the vicinity of the arbitrary point X, of the radiation Ra(X), which is incident on the additional scattering element EL toward the arbitrary point X, correspond to a distribution 91 of the primary radiation components, and a portion excluding the distribution 91 of the primary radiation components from the PSF 90 corresponds to a distribution 92 of the scattered radiation components.

Furthermore, since the energy and the like of radiation Ra used for imaging and the materials (densities and the like) and thicknesses (masses) of the top board 19 and the like, which are the additional scattering element EL, are already known, the specific shape of the PSF 90, such as the height and the half-width of a peak, are determined in advance. Accordingly, for example, the deconvolution of the distribution 92 of the scattered radiation components is performed on a radiation image obtained from imaging performed in a state where the subject Obj is not placed, so that the second characteristic h2(X) can be obtained in advance. Further, the second characteristic h2(X) is subtracted from the same radiation image or the deconvolution of the distribution 91 of the primary radiation components is performed, so that the first characteristic g2(X) can be obtained in advance.

The second estimation section 37 estimates the components of the radiation Ra, which have passed through the additional scattering element EL, by causing the scattering characteristics of the additional scattering element EL to act on the first estimation result that is the estimation result of the first estimation section 36. Specifically, radiation having a distribution represented by the first estimation result is incident on the additional scattering element EL. For this reason, the second estimation section 37 estimates the components of the radiation Ra, which have passed through the additional scattering element EL, by setting the argument of the scattering characteristics f2(X) of the additional scattering element EL as the first estimation result (f1(X)). That is, the second estimation section 37 estimates the components of the radiation Ra, which have passed through the additional scattering element EL, by calculation based on Equation 1. Since the first estimation result satisfies "f1(X)=g1(X)+h1(X)" in this embodiment, Equation 1 can be represented as Equation 2 and can be developed as Equation 3.

$$f2(f1(X))=g2(f1(X))+h2(f1(X)) \quad \text{Equation 1:}$$

$$f2(f1(X))=g2(g1(X)+h1(X))+h2(g1(X)+h1(X)) \quad \text{Equation 2:}$$

$$f2(f1(X))=g2g1(X)+g2h1(X)+h2g1(X)+h2h1(X) \quad \text{Equation 3:}$$

Figure 9:
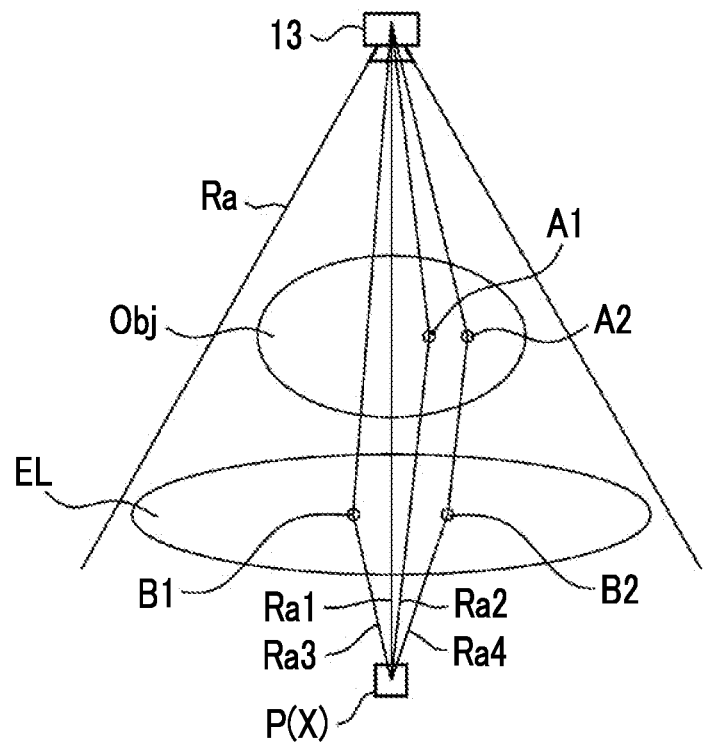
FIG. 9 is a diagram illustrating the paths of radiation reaching a pixel P(X).

As shown in FIG. 9, "g2g1(X)", which is the first term of the right side of Equation 3, represents radiation Ra1, which is transmitted through the subject Obj, is transmitted through the additional scattering element EL, and reaches a pixel P(X) positioned at an arbitrary point X, of the radiation Ra used for imaging. "g2h1(X)", which is the second term of the right side of Equation 3, represents radiation Ra2, which is scattered by a scatterer A1 included in the subject Obj, is transmitted through the additional scattering element EL, and reaches the pixel P(X) positioned at the arbitrary point X, of the radiation Ra used for imaging. "h2g1(X)", which is the third term of the right side of Equation 3, represents radiation Ra3, which is transmitted through the subject Obj, is scattered by a scatterer B1 included in the additional scattering element EL, and reaches the pixel P(X) positioned at the arbitrary point X, of the radiation Ra used for imaging. Further, "h2h1(X)", which is the fourth term of the right side of Equation 3, represents radiation Ra4, which is scattered by a scatterer A2 included in the subject Obj, is further scattered by a scatterer B2 included in the additional scattering element EL, and reaches the pixel P(X) positioned at the arbitrary point X, of the radiation Ra used for imaging.

Figure 10:
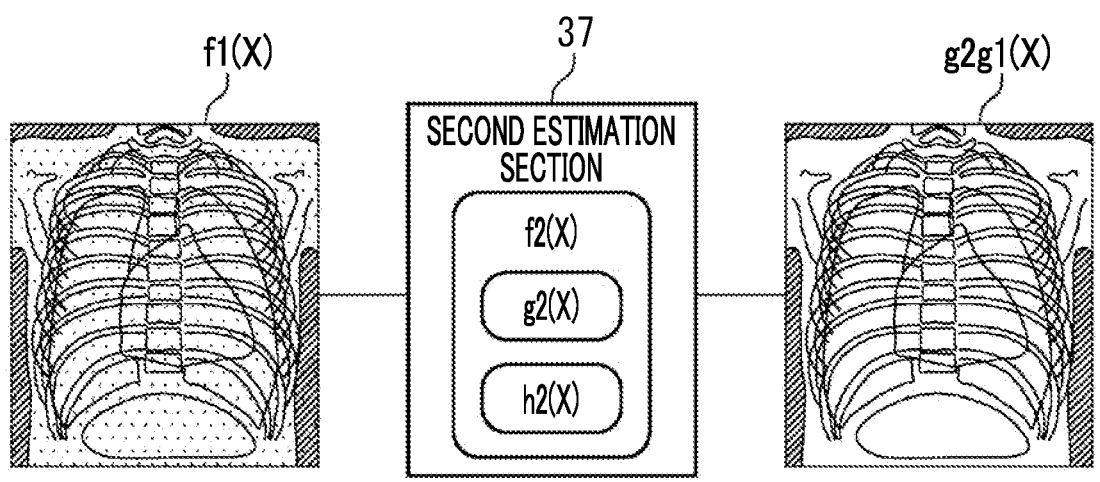
FIG. 10 is a diagram illustrating the functions of a second estimation section.

From the above description, the second estimation section 37 obtains "g2g1(X)" that is the first term of Equation 3 and/or "g2h1(X)+h2g1(X)+h2h1(X)" that is the sum of the second to fourth terms. "g2g1(X)" that is the first term of Equation 3 represents the distribution of the primary radiation components having passed through the additional scattering element EL, and "g2h1(X)+h2g1(X)+h2h1(X)" that is the sum of the second to fourth terms represents the distribution of the scattered radiation components having passed through the additional scattering element EL. In this embodiment, as shown in FIG. 10, the second estimation section 37 obtains the distribution (g2g1(X)) of the primary radiation components having passed through the additional scattering element EL and outputs the distribution (g2g1(X)) as an estimation result.

The first image generation section 38 generates the second radiation images, in which an image of the subject is formed by the radiation Ra transmitted through the subject Obj and the additional scattering element EL, using the estimation result of the second estimation section 37. In a case where the second estimation section 37 estimates the primary radiation components of the radiation Ra transmitted through the subject Obj and the additional scattering element EL, the first image generation section 38 generates the second radiation image by making an image of a second estimation result that is the estimation result of the second estimation section 37. Further, in a case where the second estimation section 37 estimates the scattered radiation components of the radiation Ra scattered by the subject Obj or the additional scattering element EL, the first image generation section 38 generates the second radiation images by subtracting the second estimation result, which is the estimation result of the second estimation section 37, from the first radiation images 51. Since the second estimation section 37 outputs the distribution of the primary radiation components having passed through the additional scattering element EL in this embodiment, the first image generation section 38 generates the second radiation image by making an image of this distribution. Accordingly, the distribution "g2g1(X)" of the primary radiation components output from the second estimation section 37 is substantially the second radiation image. The first image generation section 38 can perform various types of image processing or the like (for example, processing for adjusting contrast, processing for enhancing a structure, or the like) on the generated second radiation images as necessary.

The calculation unit 40 makes a calculation using the second radiation image that is output from the image processing unit 35. For example, the calculation unit 40 generates a so-called subtraction image using the second radiation image that is generated using the radiation image G1 obtained from the first radiation detector 15 and the second radiation image that is generated using the radiation image G2 obtained from the second radiation detector 16. The subtraction image is an enhanced image in which a specific structure included in the subject Obj is enhanced, and is generated in a case where subtraction processing of a radiation image is performed by multiplying each pixel or each region where a recognized structure is present and the attenuation coefficient μ of the structure together. In this case, each of the two second radiation images used for the subtraction processing substantially has the distribution (g2g1(X)) of the primary radiation components and the scattered radiation components are reduced with high accuracy. As a result, errors caused by the scattered radiation components are small even after the subtraction processing. Accordingly, a specific structure can be enhanced particularly accurately. The calculation unit 40 can make a calculation other than the subtraction processing. For example, the calculation unit 40 can obtain numerical values related to the composition and the like of the subject Obj, such as a bone mineral content, using a plurality of second radiation images. In this case, since the second radiation images are used, pixel values at which scattered radiation components have been reduced with high accuracy and the like can be used for calculation. Accordingly, a bone mineral content and the like can be more accurately calculated than that in a case where the pixel values are not used.

Figure 11:
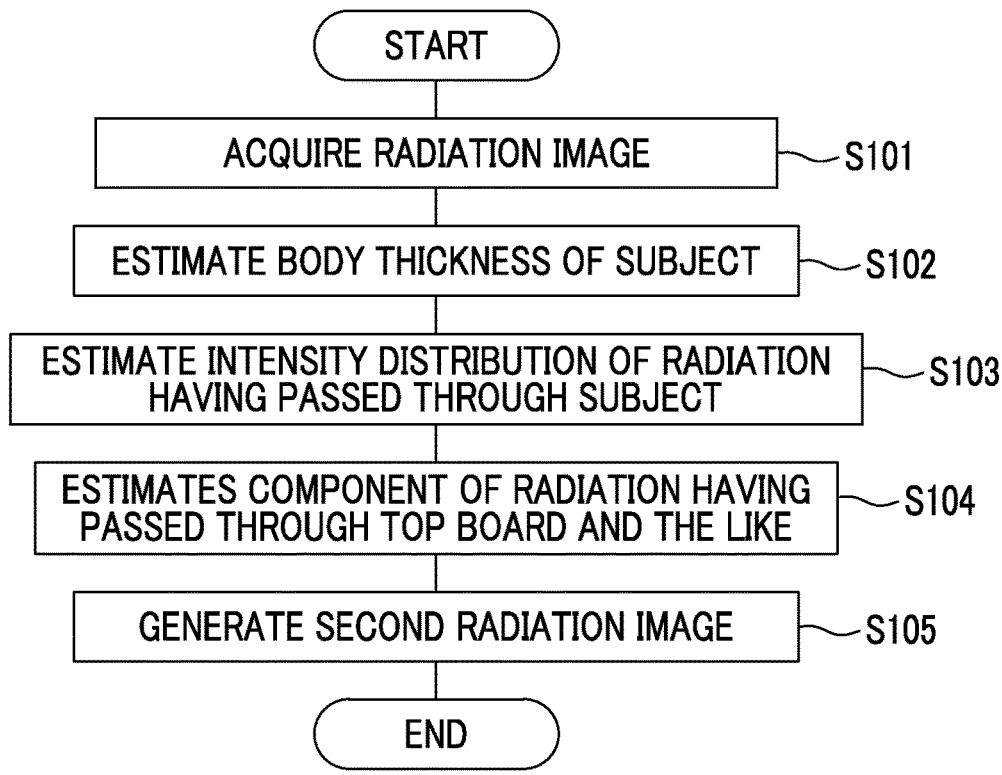
FIG. 11 is a flowchart showing the action of the radiation image processing device according to the first embodiment.

An operation (radiation image processing method) related to processing for generating the second radiation image, which is performed by the radiation image processing device 30 having the above-mentioned configuration, will be described below. As shown in FIG. 11, the radiation image acquisition unit 33 acquires the first radiation images 51 that are radiation images taken from the subject Obj using the radiation Ra (Step S101 (radiation image acquisition step)). In this embodiment, the radiation image acquisition unit 33 acquires the radiation image G1 that is taken using the first radiation detector 15 and the radiation image G2 that is taken using the second radiation detector 16, as the first radiation images 51.

In a case where the radiation image acquisition unit 33 acquires these first radiation images 51, the first estimation section 36 performs the first estimation processing on each of the first radiation images. Specifically, the first estimation section 36 estimates the body thickness of the subject Obj using the first radiation image 51 (Step S102). After that, the first estimation section 36 estimates the intensity distribution $f1(X)$ of the radiation Ra, which has passed through the subject Obj, using the estimated body thickness of the subject Obj (Step S103). The first estimation section 36 obtains the intensity distribution $f1(X)$ of the radiation Ra, which has passed through the subject Obj, by obtaining the primary radiation components $g1(X)$ having passed through the subject Obj and the scattered radiation components $h1(X)$ having passed through the subject Obj and summing up the primary radiation components $g1(X)$ and the scattered radiation components $h1(X)$. Step S102 of estimating the body thickness and Step S103 of obtaining the intensity distribution $f1(X)$ of the radiation Ra having passed through the subject Obj form a first estimation step.

After that, the second estimation section 37 estimates the components of the radiation Ra having passed through the additional scattering element EL, such as the top board 19 (Step S104 (second estimation step)). For example, the second estimation section 37 calculates the distribution $(g2g1(X))$ of the primary radiation components, which have passed through the additional scattering element EL, by causing the first characteristic $g2(X)$, which determines the distribution of the amount of radiation to be transmitted through the additional scattering element EL, to act on the intensity distribution $f1(X)$ of the radiation Ra having passed through the subject Obj. Further, the first image generation section 38 generates the second radiation image by making an image of the distribution $(g2g1(X))$ of the primary radiation components that have passed through the additional scattering element EL (Step S105 (image generation step)).

As described above, in the radiation image processing device 30, the first estimation section 36 estimates the intensity distribution $f1(X)$ of the radiation Ra having passed through the subject Obj and then the second estimation section 37 obtains the distribution $(g2g1(X))$ of the primary radiation components, which have passed through the additional scattering element EL, using the intensity distribution $f1(X)$. Further, the first image generation section 38 generates the second radiation image by making an image of this distribution, so that the second radiation image is used for the display on the display 31 or the like and/or the calculation in the calculation unit 40. That is, since the second radiation image is a radiation image that is generated through the first estimation processing and the second estimation processing in stages, scattered radiation components can be reduced with high accuracy in comparison with a radiation image in the related art (particularly, a radiation image from which scattered radiation components have been reduced by a method in the related art). That is, the radiation image processing device 30 can reduce the scattered radiation components of a radiation image by image processing more accurately than that in the related art.

In a radiation image processing device or the like in the related art, for example, the deconvolution of the distribution 92 of scattered radiation components excluding the distribution 91 of primary radiation components from a PSF 90 is performed on a first radiation image, so that scattered radiation components included in the first radiation image are may be reduced. In a case where this first method in the related art is compared with the method of performing the first estimation processing and the second estimation processing in stages, the first method in the related art is close to processing that excludes the third term $(h2g1(X))$ and the fourth term $(h2h1(X))$ of Equation 3 related to the second characteristic $h2(X)$. That is, scattered radiation component-reduction processing of the first method in the related art cannot remove the scattered radiation components of the second term $(g2h1(X))$ of Equation 3. For this reason, according to the radiation image processing device 30, scattered radiation components can be reduced with higher accuracy than the scattered radiation component-reduction processing of this first method in the related art. The reason for this is that even the scattered radiation components of the second term $(g2h1(X))$ of Equation 3 can be reduced and the primary radiation components of the first term $(g2g1(X))$ of Equation 3 can be accurately estimated.

Further, in another radiation image processing device or the like in the related art, a radiation image from which scattered radiation components have been reduced may be obtained on the basis of, for example, the estimation result of the body thickness of the subject Obj. That is, the primary radiation components $g1(X)$ having passed through the subject Obj may be used as a radiation image from which scattered radiation components have been reduced. After the primary radiation components $g1(X)$ having passed through the subject Obj are compared with the original first radiation image 51, the scattered radiation components $h1(X)$ having passed through the subject Obj are reduced. However, the first radiation image is an image that is formed by the radiation Ra having passed through not only the subject Obj but also the additional scattering element EL. For this reason, as understood from a method of estimating the primary radiation components $g1(X)$, the primary radiation components $g1(X)$ having passed through the subject Obj include scattered radiation components potentially caused by the additional scattering element EL. In a case where scattered radiation component-reduction processing of this second method in the related art is compared with the method of performing the first estimation processing and the second estimation processing in stages, the second method in the related art is close to processing for reducing the second term $(g2h1(X))$ and the fourth term $(h2h1(X))$ of Equation 3 related to the scattered radiation components $h1(X)$ having passed through the subject Obj. For this reason, according to the radiation image processing device 30, scattered radiation components can be reduced with higher accuracy than the scattered radiation component-reduction processing of this second method in the related art. The reason for this is that even the scattered radiation components of the third term $(h2g1(X))$ of Equation 3 can be reduced and the primary radiation components of the first term $(g2g1(X))$ of Equation 3 can be accurately estimated.

Furthermore, in order to improve the accuracy of image processing for reducing scattered radiation, it is usually necessary to use a processing method specialized for each radiography device. In contrast, as long as even the scattering characteristics $f2(X)$ of the additional scattering element EL are obtained in advance, the radiation image processing device 30 can generate a second radiation image by the same processing method even though the radiography device is changed. Further, the scattering characteristics f2(X) of the additional scattering element EL can also be obtained without excessive trial and error or the like from only radiography performed in a state where the subject Obj is not placed. Accordingly, accurate results can be obtained regardless of an imaging device and an imaging environment in processing for reducing scattered radiation components by a method of performing the first estimation processing and the second estimation processing in stages.

In the embodiment, the first estimation section 36 estimates the primary radiation components of the radiation Ra transmitted through the subject Obj and the scattered radiation components of the radiation Ra scattered by the subject Obj. Accordingly, the primary radiation components and the scattered radiation components, which have passed through the subject Obj, can be accurately estimated, respectively. As a result, the accuracy of the second estimation processing is improved and the accuracy of reduction of the scattered radiation components of the second radiation image is improved.

In the embodiment, the first estimation section 36 estimates the body thickness of the subject Obj using the first radiation image 51 and estimates the components of the radiation Ra, which have passed through the subject Obj, using the estimated body thickness of the subject Obj. Since the first estimation section 36 estimates the body thickness of the subject Obj in this way and uses this body thickness, the first estimation section 36 can particularly accurately estimates the components of the radiation Ra having passed through the subject Obj. Further, in the embodiment, the first estimation section 36 estimates the primary radiation components of the radiation Ra transmitted through the subject Obj and the scattered radiation components of the radiation Ra scattered by the subject Obj on the basis of the estimated body thickness of the subject Obj. Since the estimated body thickness is used to estimate the primary radiation components and the scattered radiation components having passed through the subject Obj as described above, the first estimation section 36 can particularly accurately estimates the primary radiation components and the scattered radiation components.

Furthermore, in the embodiment, the first estimation result, which is the estimation result of the first estimation section 36, is the intensity distribution f1(X) of the radiation Ra having passed through the subject Obj and the intensity distribution f1(X) includes the primary radiation components (g1(X)) of the radiation Ra transmitted through the subject Obj and the scattered radiation components (h1(X)) of the radiation Ra scattered by the subject Obj. Accordingly, all the respective terms of Equation 3 can be accurately obtained in the second estimation processing using the first estimation result. As a result, the primary radiation components and the scattered radiation components obtained in the second estimation processing are accurate.

In the embodiment, the second estimation section 37 estimates the primary radiation components of the radiation Ra (that is, the first term of Equation 3) transmitted through the subject Obj and the additional scattering element EL or the scattered radiation components of the radiation Ra (that is, the second to fourth terms of Equation 3) scattered by at least one of the subject Obj or the additional scattering element EL. For this reason, an estimation result having high accuracy is obtained.

In the embodiment, the second estimation section 37 estimates the components of the radiation Ra, which have passed through the additional scattering element EL, by causing the scattering characteristics f2(X) of the additional scattering element EL to act on the first estimation result that is the estimation result of the first estimation section 36. That is, it is taken into consideration in the second estimation processing that the radiation Ra incident on the additional scattering element EL is the radiation Ra having passed through the subject Obj. For this reason, the accuracy of the second estimation result is high.

In the embodiment, the scattering characteristics f2(X) of the additional scattering element EL specifically determine the distribution of the amount of radiation to be transmitted through the additional scattering element EL and/or the amount of radiation to be scattered by the additional scattering element EL. For this reason, in the second estimation processing, the components of the radiation Ra having passed through the additional scattering element EL can be estimated with high accuracy from the first estimation result. Further, in the embodiment, particularly, the scattering characteristics f2(X) of the additional scattering element EL include the first characteristic g2(X) that determines the distribution of the amount of radiation to be transmitted through the additional scattering element EL and the second characteristic h2(X) that determines the distribution of the amount of radiation to be scattered by the additional scattering element EL. For this reason, an accurate estimation result, in which the distribution of the amount of radiation to be transmitted through the additional scattering element EL and the distribution of the amount of radiation to be scattered by the additional scattering element EL are accurately considered, can be obtained in the second estimation processing.

It is assumed for simplification in the embodiment that radiation Ra passes through two elements, that is, the subject Obj and the additional scattering element EL, but the additional scattering element EL can be subdivided into elements and each of the elements can be considered individually. For example, it is assumed that there are two additional scattering elements, that is, the top board 19 and the gel mat (not shown) in addition to the subject Obj. Further, it is assumed that the scattering characteristics of the gel mat satisfy "$f2a(X)=g2a(X)+h2a(X)$" and the scattering characteristics of the top board 19 satisfy "$f2b(X)=g2b(X)+h2b(X)$" in order from the radiation source 13. $g2a(X)$ is a first characteristic of the gel mat and $h2a(X)$ is a second characteristic of the gel mat. Further, $g2b(X)$ is a first characteristic of the top board 19 and $h2b(X)$ is a second characteristic of the top board 19. In this case, Equation 1 of the embodiment can be extended to $f2b(f2a(f1(X)))$. That is, the second estimation section 37 can estimate primary radiation components ($g2bg2af1(X)$), which are transmitted through the subject Obj, the gel mat, and the top board 19, by causing the scattering characteristics $f2a(X)$ of the gel mat and the scattering characteristics $f2b(X)$ of the top board 19 to act on the first estimation result ($f1(X)$) in order of passage of the radiation Ra. The same applies to a case where there are three or more additional scattering elements EL, and the second estimation section 37 can more accurately estimate the primary radiation components by causing the scattering characteristics of the respective additional scattering elements to act on the first estimation result ($f1(X)$) in order of passage of the radiation Ra.

Furthermore, the radiation Ra passes through the subject Obj first in the embodiment, but the scattered radiation component-reduction processing of the radiation image processing device 30 can be extended and applied even in a case where the additional scattering element EL is positioned between the radiation source 13 and the subject Obj. For example, it is assumed that a scattering element (not shown. Hereinafter, referred to as a pre-scattering element) having scattering characteristics [f0(X)=g0(X)+h0(X)] is positioned between the radiation source 13 and the subject Obj and an additional scattering element EL through which the radiation Ra is to passes is positioned after the subject Obj. g0(X) is a first characteristic of the pre-scattering element positioned before the subject Obj, and h0(X) is a second characteristic of the pre-scattering element positioned before the subject Obj. In this case, in a case where the first estimation section 36 is to obtain the first estimation result (f1(X)) from the first radiation image 51, radiation having passed through the pre-scattering element having the scattering characteristics f0(X) is incident on the first estimation section 36 and the first estimation section 36 obtains the first estimation result. That is, Equation 1 of the embodiment is extended to f2(f1(f0(X))) as a whole. Accordingly, even in a case where the pre-scattering element is positioned before the subject Obj, a second radiation image from which scattered radiation components have been accurately reduced can be obtained.

The embodiment, the modification example, and the like can be used in a state where some or all of the embodiment, the modification example, and the like are arbitrarily combined. Further, the content of the specific processing for estimating primary radiation components and scattered radiation components of the embodiment and the like is an example, and processing for estimating primary radiation components and scattered radiation components of another aspect can be applied in stages according to the embodiment and the like. Furthermore, the radiation image processing device 30 of the embodiment and the like can use a radiation image that is taken from an arbitrary subject Obj (including a case where the subject is an animal or an object) and a portion to be imaged of the arbitrary subject Obj.

The embodiment and the like include a radiation image processing method comprising: a step of acquiring a first radiation image 51, which is taken from the subject Obj, using radiation Ra by the radiation image acquisition unit 33; a step of estimating components of the radiation Ra, which have passed through the subject Obj, using the first radiation image 51 by the first estimation section 36; a step of estimating components of the radiation Ra, which have passed through the additional scattering element EL, using an estimation result of the first estimation section 36 and scattering characteristics f2(X) of the additional scattering element EL, through which the radiation Ra further passes after passing through the subject Obj, by the second estimation section 37; and a step of generating a second radiation image, in which an image of the subject Obj is formed by the radiation Ra transmitted through the subject Obj and the additional scattering element EL, using an estimation result of the second estimation section 37 by the first image generation section 38.

Further, a program uses a computer or some components of the computer to execute: a radiation image acquisition step of acquiring a first radiation image 51, which is taken from the subject Obj, using radiation Ra; a first estimation step of estimating components of the radiation Ra, which have passed through the subject Obj, using the first radiation image 51; a second estimation step of estimating components of the radiation Ra, which have passed through the additional scattering element EL, using an estimation result of the first estimation step and scattering characteristics f2(X) of the additional scattering element EL through which the radiation Ra further passes after passing through the subject Obj; and a image generation step of generating a second radiation image, in which an image of the subject Obj is formed by the radiation Ra transmitted through the subject Obj and the additional scattering element EL, using an estimation result of the second estimation step. The program forms the radiation image processing device 30.

Second Embodiment

Figure 12:
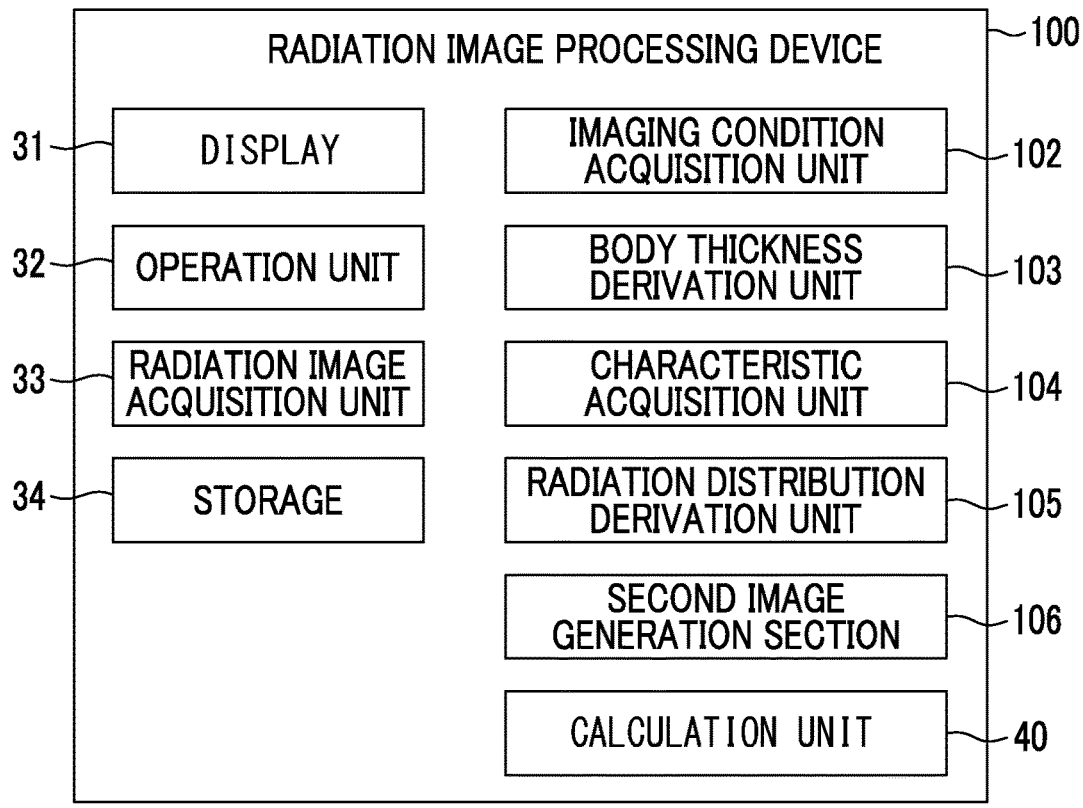
FIG. 12 is a block diagram showing the configuration of a radiation image processing device according to a second embodiment.
Figure 13:
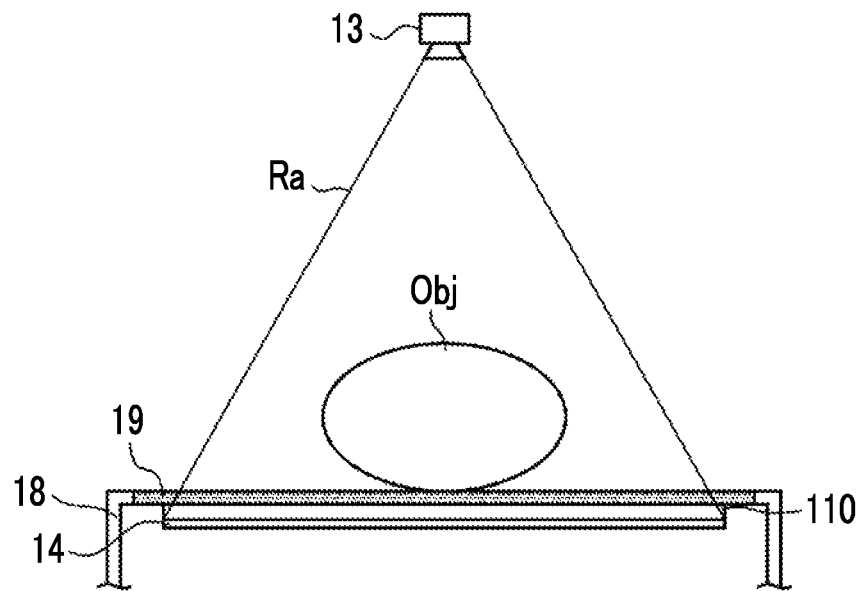
FIG. 13 is a diagram illustrating an imaging table and a grid that are positioned between a subject and a radiography panel.

In a radiography system of a second embodiment, a radiation image processing device 100 shown in FIG. 12 is used instead of the radiation image processing device 30 according to the first embodiment. The radiation image processing device 100 comprises a radiation image acquisition unit 33, an imaging condition acquisition unit 102, a body thickness derivation unit 103, a characteristic acquisition unit 104, a radiation distribution derivation unit 105, and a second image generation section 106. The radiation image processing device according to the embodiment of the invention may have both the function of the radiation image processing device 30 according to the first embodiment and the function of the radiation image processing device 100 according to the second embodiment.

In the radiation image processing device 100, programs related to various types of processing are incorporated in a program memory. The programs incorporated in the program memory are executed by a central controller (not shown) formed of a processor, so that the functions of the radiation image acquisition unit 33, the imaging condition acquisition unit 102, the body thickness derivation unit 103, the characteristic acquisition unit 104, the radiation distribution derivation unit 105, and the second image generation section 106 are realized.

The radiation image acquisition unit 33 drives the radiation source 13 to irradiate a subject Obj with radiation, and detects the radiation transmitted through the subject Obj by the radiography panel 14 to acquire a radiation image G0 of the subject Obj. In the second embodiment, a grid 110 and the top board 19 of the imaging table 18 are interposed between the subject Obj and the radiography panel 14. For this reason, the radiation transmitted through the subject Obj is transmitted through the top board 19 and the grid 110, and the radiography panel 14 is irradiated with the radiation. It is preferable that the grid described in the first embodiment is used as the grid 110.

In a case where the subject Obj is to be imaged, imaging conditions are set. The quality and dose of radiation and an imaging distance at the time of imaging (source-to-image receptor distance (SID)) are used as the imaging conditions. The quality of radiation is defined using one or more of the total capacity of filtration [mmAI equivalent], a half-value layer [mmAI], and a tube voltage [kV] of a radiation generator of the radiation source 13. The tube voltage means the maximum value of the distribution of radiation energies to be generated. The total capacity of filtration is obtained from the conversion of the capacity of filtration of each of components forming the radiation generator, a collimator, and the like of the radiation source 13 into the thickness of aluminum. As the total capacity of filtration is larger, the influence of beam hardening is greater and there are more high-energy components in the wavelength distribution of radiation. The half-value layer is defined by the thickness of aluminum that is required to attenuate a dose in half in the distribution of generated radiation energies. As the thickness of aluminum of the half-value layer is larger, there are more high-energy components in the wavelength distribution of radiation.

The dose is defined using any one of a tube current-time product [mAs] and an irradiation dose [mR] of the radiation generator of the radiation source 13. Further, SID is a distance [cm] between the radiation source 13 and the radiography panel 14.

At the time of imaging the subject Obj, imaging conditions are determined depending on an imaging technique. For this reason, in this embodiment, a table in which various imaging techniques and imaging conditions are associated with each other is stored in a storage 34 in advance. In a case where an operator designates an imaging technique input from the operation unit 32 at the time of imaging, the table stored in the storage 34 is referred, imaging conditions corresponding to the imaging technique are read from the table, and the subject Obj is imaged according to the read imaging conditions. The imaging conditions used at the time of imaging are temporarily stored in the storage 34. The imaging conditions are not limited to the imaging conditions corresponding to the imaging technique, and may be imaging conditions that are designated by the operator's input using the operation unit 32.

The imaging condition acquisition unit 102 reads out the imaging conditions, which are used at the time of imaging the subject, from the storage 34 to acquire the imaging conditions.

The body thickness derivation unit 103 derives the body thickness distribution of the subject Obj on the basis of the radiation image G0 and the imaging conditions. Hereinafter, the body thickness distribution derived by the body thickness derivation unit 103 will be referred to as an initial body thickness distribution t0. The derivation of an initial body thickness distribution t0 will be described below.

First, in a case where the radiation source 13 is driven to irradiate the radiography panel 14 with radiation in a state where the subject Obj is not present, a reaching dose I0(x,y) of radiation, which is emitted from the radiation source 13 and reaches the radiography panel 14, is represented by equation (X1) to be described below. In Equation (X1), mAs included in the imaging conditions is a tube current-time product and kV is a tube voltage. In a case where a half-value layer is also considered, a reaching dose I0(x,y) is represented by Equation (X1-1) to be described below. Here, F is a non-linear function that represents the amount of radiation reaching the radiography panel 14 in a case where the radiography panel 14 is irradiated with radiation having a reference dose (for example, 1 mAs) at a reference SID (for example, 100 cm) in a state where the subject Obj is not present. F is changed depending on each tube voltage or a tube voltage and a half-value layer. Further, since a reaching dose I0 is derived for each pixel of a radiation image acquired by the radiography panel 14, (x,y) means represents the pixel position of each pixel. Furthermore, in the following description, mmAl will be included in the parentheses in each equation as shown in Equation (X1-2) to be described below in order to include both a case where a half-value layer is considered and a case where a half-value layer is not considered.

$$I0(x, y) = mAs \times F(kV)/SID^2 \quad (X1)$$

$$I0(x, y) = mAs \times F(kV, mmAl)/SID^2 \quad (X1-1)$$

$$I0(x, y) = mAs \times F(kV(, mmAl))/SID^2 \quad (X1-2)$$

Further, in a case where an initial body thickness distribution is denoted by t0, the attenuation coefficient of a subject Obj having an initial body thickness distribution t0 is denoted by $\mu(t0)$, and a scatter-to-primary ratio, which is a ratio between the amount of scattered radiation and the amount of primary radiation included in radiation having been transmitted through the subject Obj having an initial body thickness distribution t0 in a case where the spread of scattered radiation is not considered, is denoted by STPR (t0), a dose I1 of radiation having been transmitted through the subject Obj is represented by Equation (X2) to be described below. In Equation (X2), an initial body thickness distribution t0, a reaching dose I0, and a dose I1 are derived for each pixel of the radiation image G0 but (x,y) is omitted. Further, STPR is a non-linear function depending on not only a body thickness but also a tube voltage [kV] and a half-value layer [mmAl], but kV and mmAl are omitted in Equation (X2).

$$I1 = I0 \times \exp\{-\mu(t0) \times t0\} \times \{1 + STPR(t0)\} \quad (X2)$$

In Equation (X2), a dose I1 is the pixel value of each pixel of the radiation image G0 and a reaching dose I0 is derived by Equations (X1) and (X1-1). On the other hand, since F and STPR are non-linear functions, Equation (X2) cannot be solved algebraically with respect to t0. For this reason, the body thickness derivation unit 103 defines an error function E1 shown in Equation (X3) or Equation (X3-1) to be described below. Further, t0 at which the error function E1 is minimum or the error function E1 is less than a predetermined threshold value Th1 is derived as an initial body thickness distribution. In this case, the body thickness derivation unit 103 derives an initial body thickness distribution t0 using an optimization algorithms, such as a steepest descent method and a conjugate gradient method.

$$E1 = [I1 - I0 \times \exp\{-\mu(t0) \times t0\} \times \{1 + STPR(t0)\}]^2 \quad (X3)$$

$$E1 = |I1 - I0 \times \exp\{-\mu(t0) \times t0\} \times \{1 + STPR(t0)\}| \quad (X3-1)$$

The characteristic acquisition unit 104 acquires the radiation characteristics of an element that is interposed between the subject Obj and the radiography panel 14 at the time of imaging. Here, radiation transmittance is changed depending on the quality of the radiation having been transmitted through the subject Obj in a case where the radiation having been transmitted through the subject Obj is transmitted through the element interposed between the subject Obj and the radiography panel 14. Further, primary radiation and scattered radiation, which are included in the radiation having been transmitted through the subject Obj, are different from each other in transmittance due to a difference in the travel direction and quality of radiation. For this reason, the primary radiation transmittance and the scattered radiation transmittance of an element are used as the radiation characteristics of the element in the second embodiment.

As described above, radiation transmittance is changed depending on the quality of the radiation having been transmitted through the subject Obj in a case where the radiation having been transmitted through the subject Obj is transmitted through the element interposed between the subject Obj and the radiography panel 14. Further, the quality of the radiation having been transmitted through the subject Obj depends on the body thickness t of the subject Obj. For this reason, the primary radiation transmittance and the scattered radiation transmittance can be denoted by Tp(t) and Ts(t), respectively, as functions of the body thickness t of the subject Obj.

The quality of the radiation having been transmitted through the subject Obj also depends on the quality of radiation of the radiation source 13 that is included in the imaging conditions. The quality of radiation depends on a tube voltage and a half-value layer. For this reason, the primary radiation transmittance and the scattered radiation transmittance are exactly denoted by Tp(kV(,mmAl),t) and Ts(kV(,mmAl),t), respectively. In the following description, the primary radiation transmittance and the scattered radiation transmittance may be simply denoted by Tp and Ts, respectively.

Here, the primary radiation transmittance Tp and the scattered radiation transmittance Ts of the element, which is interposed between the subject Obj and the radiography panel 14, depend on the body thickness t of the subject Obj as described above. For this reason, in the second embodiment, the primary radiation transmittance Tp and the scattered radiation transmittance Ts of an element corresponding to the body thickness of the subject Obj may be measured using phantoms that have various thicknesses imitating the body thickness t of the subject Obj, and a table, in which a relationship between the body thickness t of the subject Obj and the primary radiation transmittance Tp and the scattered radiation transmittance Ts of an element is defined, may be generated on the basis of measurement results and may be stored in the storage 34. The measurement of the primary radiation transmittance Tp and the scattered radiation transmittance Ts of an element corresponding to the body thickness t of the subject Obj will be described below.

Figure 14:
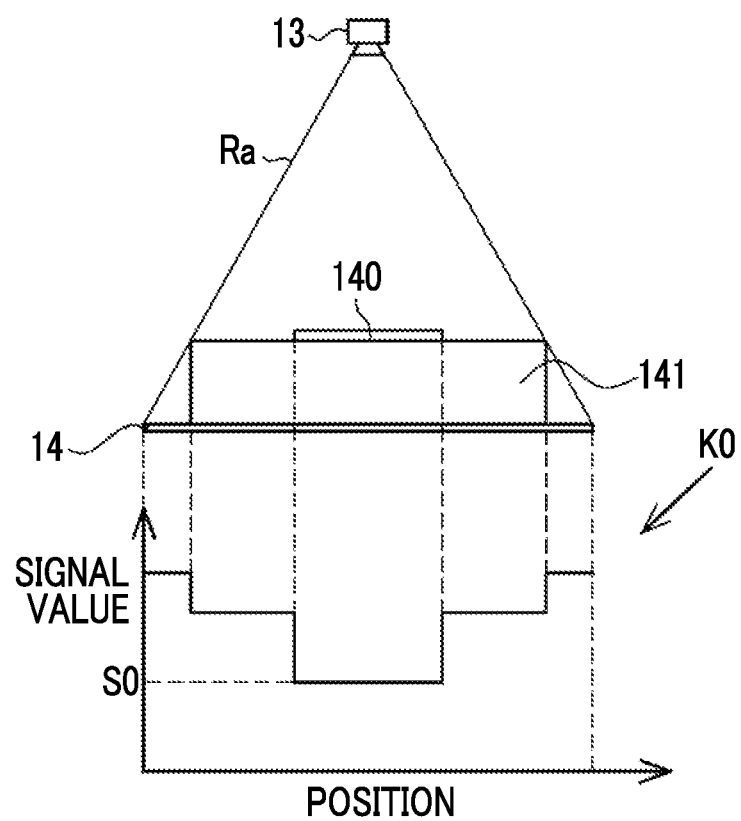
FIG. 14 is a diagram illustrating a method of measuring scattered radiation transmittance in a case where a top board and a grid are not provided.
Figure 15:
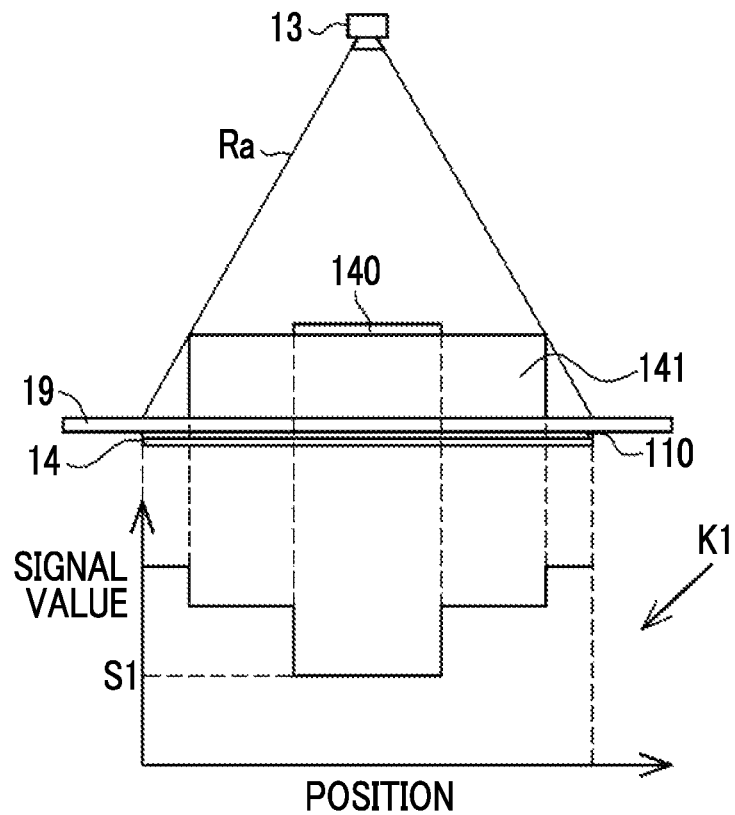
FIG. 15 is a diagram illustrating a method of measuring scattered radiation transmittance in a case where a top board and a grid are provided.

First, the calculation of the scattered radiation transmittance Ts will be described. FIGS. 14 and 15 are diagrams illustrating the measurement of scattered radiation transmittance Ts corresponding to the body thickness of the subject Obj. First, as shown in FIG. 14, a phantom 141 imitating a human body is placed on the surface of the radiography panel 14 and a lead plate 140 is further placed on the phantom 141. Here, phantoms 141 have various thicknesses, such as 5 cm, 10 cm, and 20 cm, and are made of a material, such as acrylic, having the same radiation transmittance as, for example, water. The radiation source 13 is driven to irradiate the radiography panel 14 with radiation in this state, so that the characteristic acquisition unit 104 acquires a radiation image K0 for measurement. The signal value of the radiation image K0 is large in the region of the radiography panel 14 directly irradiated with radiation and is reduced in an order of the region of the phantom 141 and the region of the lead plate 140.

Since the lead plate 140 does not transmit radiation, a signal value will be 0 in a region of the radiation image K0 corresponding to the lead plate 140. However, radiation scattered by the phantom 141 reaches a region corresponding to the lead plate 140 placed above the radiography panel 14. For this reason, the region of the radiation image K0 corresponding to the lead plate 140 has a signal value S0 corresponding to scattered radiation components caused by the phantom 141.

Next, as shown in FIG. 15, a phantom 141 is placed on the top board 19 and the lead plate 140 is placed on the phantom 141. Then, the radiation source 13 is driven to irradiate the radiography panel 14 with radiation in a state where the radiography panel 14 and the grid 110 are disposed below the top board 19 as in a case where the subject Obj is imaged. As a result, the characteristic acquisition unit 104 acquires a radiation image K1 for measurement. As in a case of the radiation image K0, the signal value of the radiation image K1 is large in the region of the radiography panel 14 directly irradiated with radiation and is reduced in an order of the region of the phantom 141 and the region of the lead plate 140. Here, in a case where imaging is performed in a state where the top board 19 and the grid 110 are interposed between the phantom 141 and the radiography panel 14 as shown in FIG. 15, not only radiation scattered by the phantom 141 but also radiation scattered by the top board 19 and the grid 110 reaches a region corresponding to the lead plate 140 placed above the radiography panel 14. For this reason, the region of the radiation image K1 corresponding to the lead plate 140 has a signal value S1 corresponding to scattered radiation components caused by the phantom 141, the top board 19, and the grid 110.

Since the signal value S1 includes scattered radiation components caused by the top board 19 and the grid 110, the signal value S1 is larger than the signal value S0 shown in FIG. 14. Accordingly, the scattered radiation transmittance Ts of an element, which is interposed between the subject Obj and the radiography panel 14 in a case where a phantom 141 having a thickness t is imaged, that is, the top board 19 and the grid 110 can be calculated from "S1/S0".

Figure 16:
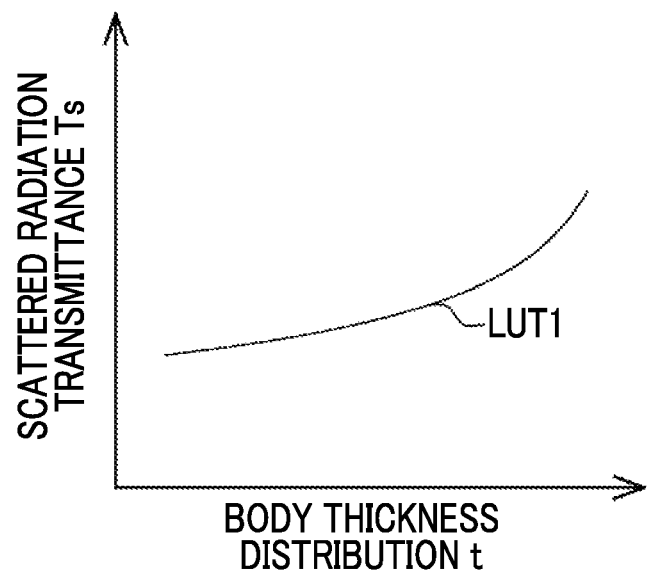
FIG. 16 is a graph showing a relationship between the body thickness distribution of the subject and scattered radiation transmittance.

In the second embodiment, the characteristic acquisition unit 104 uses at least two types of phantoms having different thicknesses to calculate scattered radiation transmittance Ts corresponding to each of the thicknesses as shown in FIGS. 14 and 15. Further, the characteristic acquisition unit 104 derives scattered radiation transmittance Ts corresponding to a thickness, which is not obtained from phantoms 141, by interpolating scattered radiation transmittance Ts corresponding to a plurality of measured thicknesses. Accordingly, the characteristic acquisition unit 104 generates a table LUT1, which shows a relationship between the body thickness distribution t of the subject Obj and the scattered radiation transmittance Ts of an element interposed between the subject Obj and the radiography panel 14 as shown in FIG. 16, by interpolating scattered radiation transmittance corresponding to a thickness between the respective thicknesses.

Figure 17:
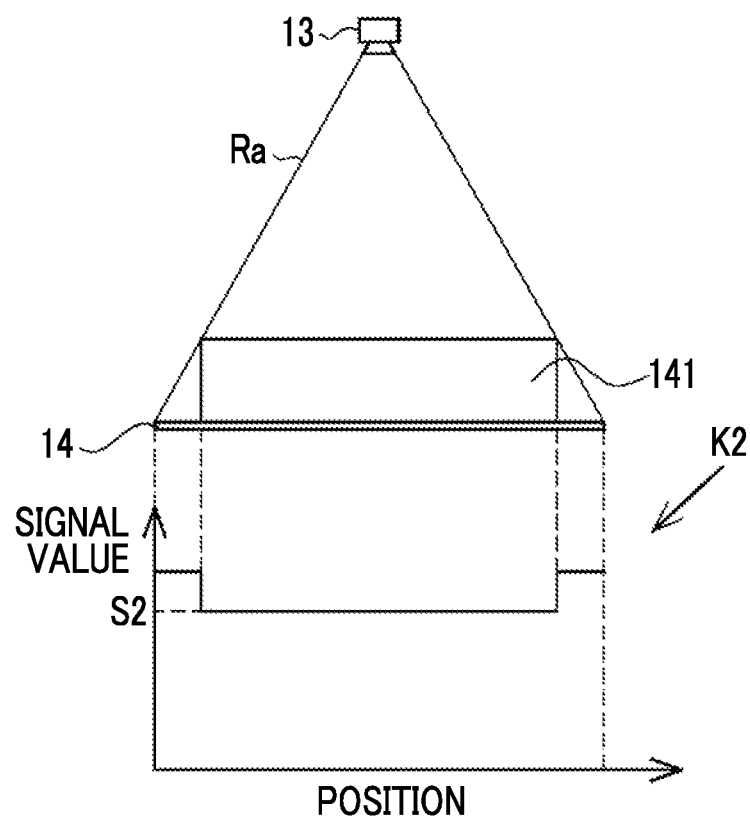
FIG. 17 is a diagram illustrating a method of measuring primary radiation transmittance in a case where a top board and a grid are not provided.
Figure 18:
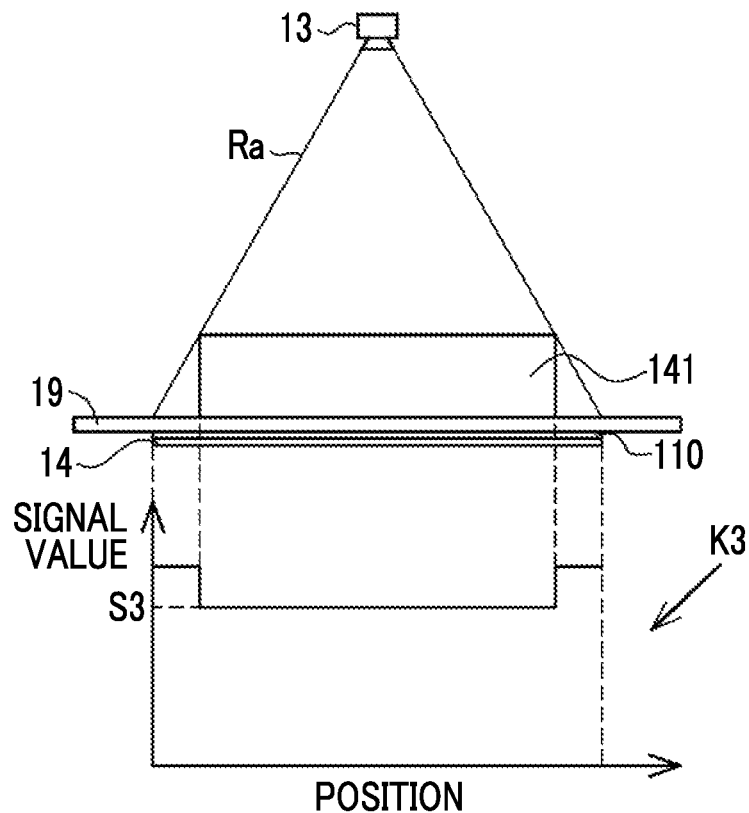
FIG. 18 is a diagram illustrating a method of measuring primary radiation transmittance in a case where a top board and a grid are provided.

Next, the calculation of primary radiation transmittance will be described. FIGS. 17 and 18 are diagrams illustrating the measurement of primary radiation transmittance Tp corresponding to the body thickness of the subject Obj. First, as shown in FIG. 17, a phantom 141 imitating a human body is placed on the surface of the radiography panel 14. Here, the same phantoms as the phantoms used in the case where scattered radiation transmittance Ts is derived are used as phantoms 141. Then, the radiation source 13 is driven to irradiate the radiography panel 14 with radiation in this state, so that the characteristic acquisition unit 104 acquires a radiation image K2 for measurement. A signal value S2 of a region of the radiation image K2 corresponding to the phantom 141 includes both primary radiation components and scattered radiation components of radiation transmitted through the phantom 141. Here, the scattered radiation components of radiation transmitted through the phantom 141 are the signal value S0 of the radiation image K0 that is obtained by the method shown in FIG. 14. For this reason, the primary radiation components of radiation transmitted through the phantom 141 are derived by "S2-S0".

Next, as shown in FIG. 18, a phantom 141 is placed on the top board 19 and the radiation source 13 is driven to irradiate the radiography panel 14 with radiation in a state where the radiography panel 14 and the grid 110 are placed below the top board 19 as in a case where the subject Obj is imaged. As a result, the characteristic acquisition unit 104 acquires a radiation image K3 for measurement. A signal value S3 of a region of the radiation image K3 corresponding to the phantom 141 includes both primary radiation components and scattered radiation components of radiation transmitted through the phantom 141 and the top board 19 and the grid 110. Here, the scattered radiation components of radiation transmitted through the phantom 141, the top board 19 and the grid 110 are the signal value S1 of the radiation image K1 that is obtained by the method shown in FIG. 15. For this reason, the primary radiation components of radiation transmitted through the phantom 141, the top board 19, and the grid 110 are derived by "S3-S1".

Figure 19:
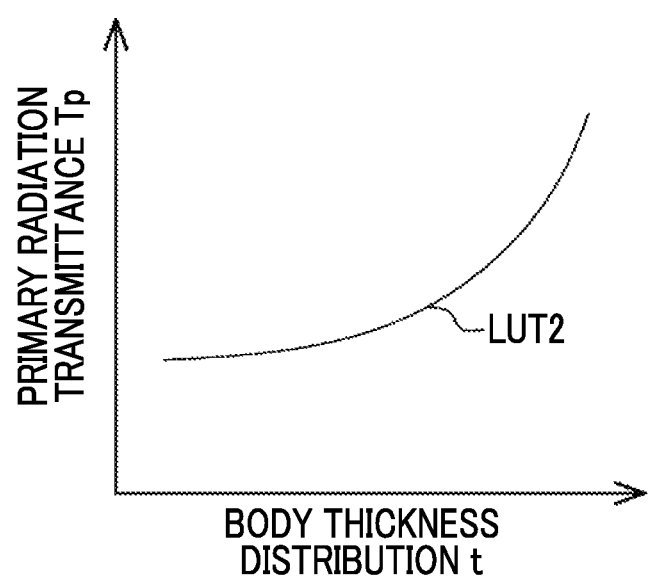
FIG. 19 is a graph showing a relationship between the body thickness distribution of the subject and primary radiation transmittance.

Accordingly, the primary radiation transmittance Tp of the top board 19 and the grid 110, which are interposed between the subject Obj and the radiography panel 14 in a case where the phantom 141 is imaged, can be calculated from "(S3-S1)/(S2-S0)". Further, in the second embodiment, the characteristic acquisition unit 104 uses at least two types of phantoms having different thicknesses to calculate primary radiation transmittance Tp corresponding to each of the thicknesses as shown in FIGS. 17 and 18. Furthermore, the characteristic acquisition unit 104 derives primary radiation transmittance Tp corresponding to a thickness, which is not obtained from phantoms 141, by interpolating primary radiation transmittance Tp corresponding to a plurality of measured thicknesses. Accordingly, the characteristic acquisition unit 104 generates a table LUT2 that shows a relationship between the body thickness distribution t of the subject Obj and the primary radiation transmittance Tp of an element interposed between the subject Obj and the radiography panel 14 as shown in FIG. 19.

The table LUT1 (first table) and the LUT2 (second table) generated as described above are stored in the storage 34. The table is generated according to various imaging conditions (that is, the quality of radiation, a dose, and a radiation source distance) and the type of the grid 110 to be used, and is stored in the storage 34.

The characteristic acquisition unit 104 acquires primary radiation transmittance Tp(t0) and scattered radiation transmittance Ts(t0) of an element, which is interposed between the subject Obj and the radiography panel 14, corresponding to the initial body thickness distribution t0 with reference to the tables LUT1 and LUT2, which are stored in the storage 34, according to the imaging conditions that are acquired by the imaging condition acquisition unit 102. Since the primary radiation transmittance Tp and the scattered radiation transmittance Ts depend on the quality of radiation, the primary radiation transmittance Tp and the scattered radiation transmittance Ts can be denoted by Tp(kV(,mmAI),t0) and Ts(kV(,mmAI),t0), respectively.

The radiation distribution derivation unit 105 derives the primary radiation distribution and the scattered radiation distribution of radiation that is detected by the radiography panel 14, using the imaging conditions, the body thickness distribution, and the radiation characteristics of an element interposed between the subject Obj and the radiography panel 14. Here, a primary radiation distribution Ip0 and a scattered radiation distribution Is0 of the radiation having been transmitted through the subject Obj are represented by Equations (X4) and (X5) to be described below in a case where the body thickness distribution is denoted by t. PSF of Equation (X5) is a point spread function showing the distribution of scattered radiation spreading from one pixel, and is defined according to the quality of radiation and a body thickness. Further, * represents convolution. The primary radiation distribution Ip0 and the scattered radiation distribution Is0 are derived for each pixel of the radiation image G0 but (x,y) is omitted in the Equations (X4) and (X5). Further, the body thickness distribution, the primary radiation distribution Ip0, and the scattered radiation distribution Is0 are repeatedly derived as described later in the second embodiment, but the initial body thickness distribution t0 is used as the body thickness distribution t in a case where the first derivation of the primary radiation distribution Ip0 and the scattered radiation distribution Is0 is performed.

$$Ip0 = I0 \times \exp\{-\mu(t) \times t\} \tag{X4}$$

$$Is0 = Ip0 \times STPR(kV(, mmA1), t) * PSF(kV(, mmA1), t) \tag{X5}$$

In addition, the radiation distribution derivation unit 105 derives a primary radiation distribution Ip1 and a scattered radiation distribution Is1 of radiation, which reaches the radiography panel 14, by Equations (X6) and (X7), which will be described below, using the primary radiation transmittance Tp and the scattered radiation transmittance Ts of an element that is interposed between the subject Obj and the radiography panel 14. Further, the primary radiation distribution Ip1 and the scattered radiation distribution Is1 of radiation reaching the radiography panel 14 are derived by Equations (X6) and (X7) to be described below. Furthermore, the sum Iw1 of the primary radiation distribution Ip1 and the scattered radiation distribution Is1 is derived by Equation (X8) to be described below. Even in Equations (X6) and (X7), the initial body thickness distribution t0 is used as the body thickness distribution t in a case where the first derivation of the primary radiation distribution Ip1 and the scattered radiation distribution Is1 is performed.

$$Ip1 = Ip0 \times Tp(kV(, mmA1), t) \tag{X6}$$

$$Is1 = Is0 \times Ts(kV(, mmA1), t) \tag{X7}$$

$$Iw1 = Ip1 + Is1 \tag{X8}$$

The second image generation section 106 derives an error E2 between the sum Iw1 of the primary radiation distribution Ip1 and the scattered radiation distribution Is1 and a dose, that is, a pixel value I1 at each pixel position in the radiation image G0. The derivation of the error E2 is performed by Equation (X9) or (X9-1) to be described below. In Equation (X9) or (X9-1), N denotes the number of pixels of the radiation image G0 and Σ represents the sum about all pixels of the radiation image G0. Since Equation (X9-1) calculates "I1/Iw1" in the log, Equation (X9-1) can derive the error E2 without depending on the dose of radiation with which the subject Obj is irradiated, that is, a reaching dose I0.

$$E2 = (1/N) \times \sum \{I1 - Iw1\}^2 \tag{X9}$$

$$E2 = (1/N) \times \sum |\log\{I1/Iw1\}| \qquad (X9\text{-}1)$$

Then, the second image generation section 106 updates the body thickness distribution t so that the error E2 is minimum or the error E2 is less than a predetermined threshold value Th2. Then, the second image generation section 106 repeats the acquisition of the primary radiation transmittance Tp and the scattered radiation transmittance Ts and the derivation of the primary radiation distribution Ip1 and the scattered radiation distribution Is1 based on the updated body thickness distribution. Here, the calculation performed by the second image generation section 106 is referred to as repeated calculation. In the second embodiment, the second image generation section 106 performs repeated calculation so that the error E2 is less than the predetermined threshold value Th2. Then, the second image generation section 106 outputs a processed radiation image Gm that has a primary radiation distribution Ipm derived on the basis of a body thickness distribution tm of the subject Obj where the error E2 is less than the predetermined threshold value Th2 as pixel values.

Figure 20:
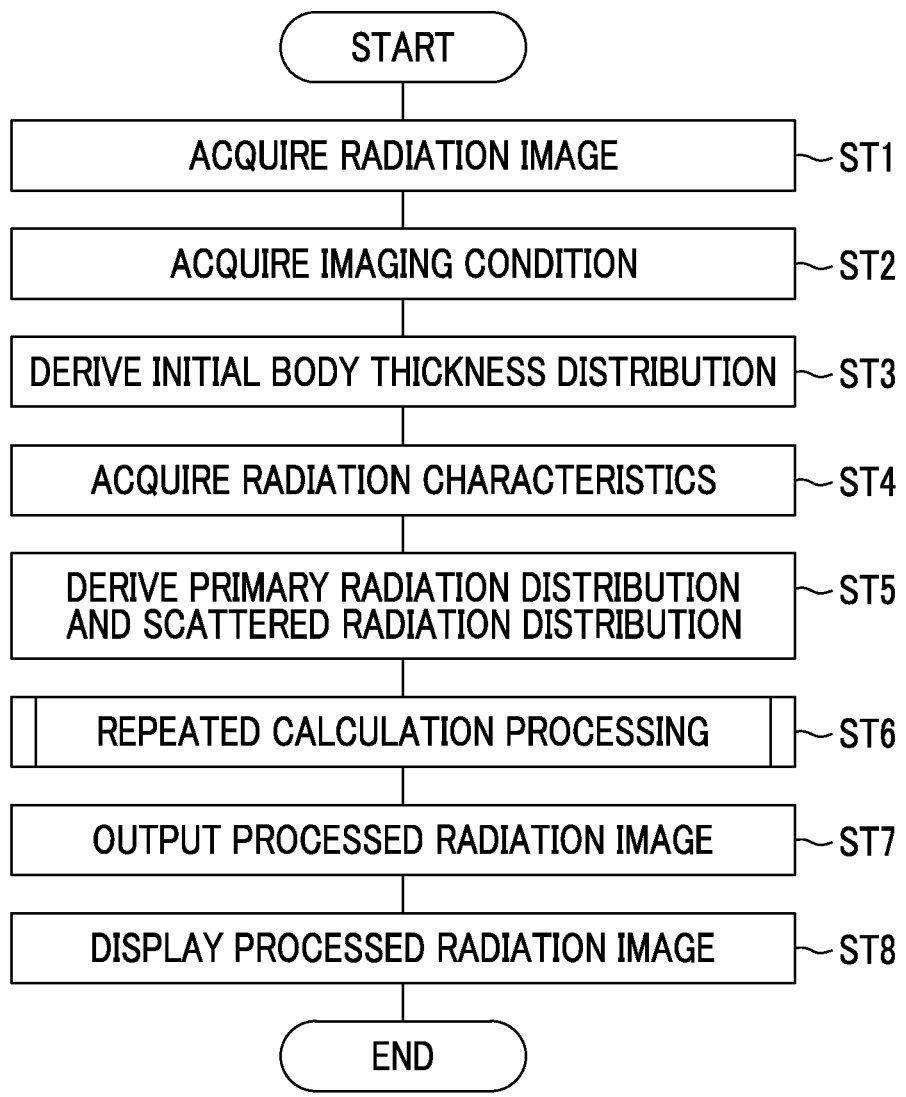
FIG. 20 is a flowchart showing the action of the radiation image processing device according to the second embodiment.

Next, processing performed in the second embodiment will be described with reference to a flowchart of FIG. 20. It is assumed that the radiation image G0 is acquired from imaging and is stored in the storage 34. In a case where an instruction to start processing is input from the operation unit 32, the radiation image acquisition unit 33 acquires the radiation image G0 from the storage 34 (Step ST1). Then, the imaging condition acquisition unit 102 acquires imaging conditions at the time of imaging the subject Obj (Step ST2). After that, the body thickness derivation unit 103 derives the initial body thickness distribution t0 on the basis of the radiation image G0 and the imaging conditions (Step ST3). Further, the characteristic acquisition unit 104 acquires the radiation characteristics, that is, the primary radiation transmittance Tp and the scattered radiation transmittance Ts of an element that is interposed between the subject Obj and the radiography panel 14 (Step ST4). Subsequently, the radiation distribution derivation unit 105 derives the primary radiation distribution Ip1 and the scattered radiation distribution Is1 of radiation, which is detected by the radiography panel 14, using the imaging conditions, the body thickness distribution, and the radiation characteristics of an element that is interposed between the subject Obj and the radiography panel 14 (Step ST5). As described above, the processing of Steps ST3 to ST5 is performed on the basis of the initial body thickness distribution to.

Figure 21:
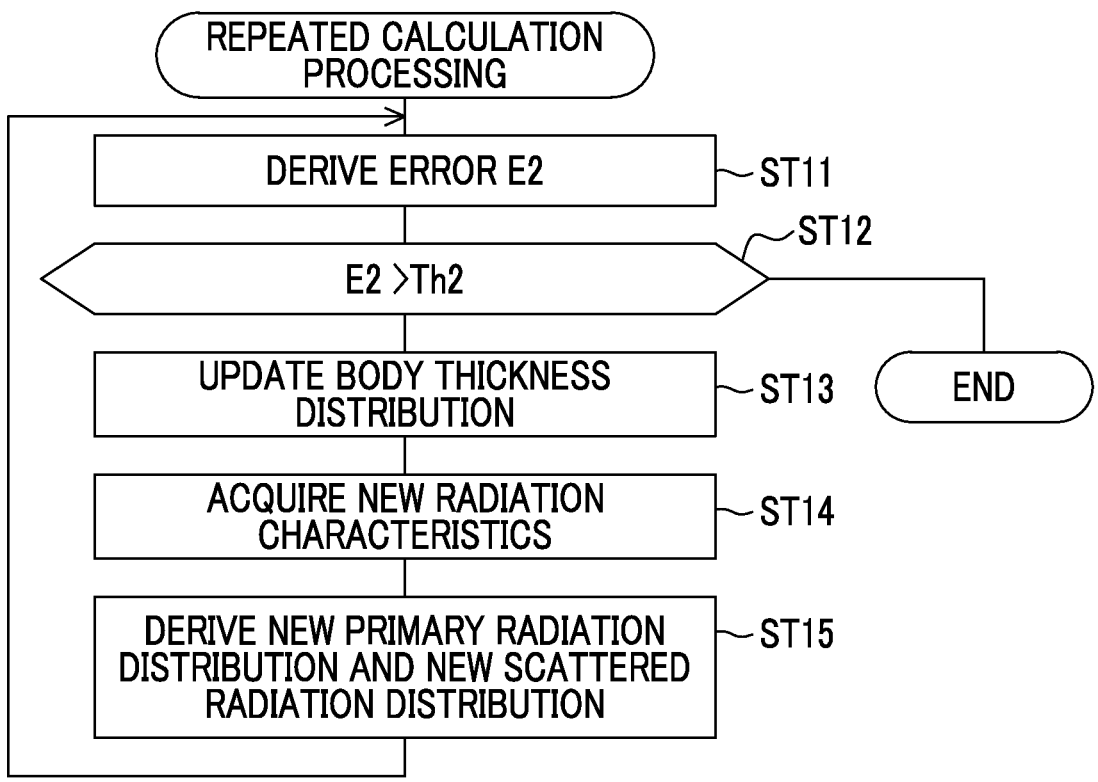
FIG. 21 is a flowchart showing repetitive processing.

Next, the second image generation section 106 performs repeated calculation processing (Step ST6). The flow of repeated calculation will be described with reference to a flowchart of FIG. 21. First, the second image generation section 106 derives the error E2 between the sum Iw1 of the primary radiation distribution Ip1 and the scattered radiation distribution Is1 and a pixel value I1 at each position in the radiation image G0 (Step ST11). Then, the second image generation section 106 determines whether or not the error E2 is less than a predetermined threshold value Th2 (Step ST12). In a case where the error E2 is not less than the predetermined threshold value Th2 in Step ST12, the second image generation section 106 updates the body thickness distribution t so that the error E2 is reduced (Step ST13). Then, the characteristic acquisition unit 104 acquires new radiation characteristics, that is, new primary radiation transmittance Tp and new scattered radiation transmittance Tp on the basis of the updated body thickness distribution t (Step ST14). Further, the radiation distribution derivation unit 105 derives a new primary radiation distribution Ip1 and a new scattered radiation distribution Is1 (Step ST15). Then, the second image generation section 106 returns to the processing of Step ST11 and repeats the processing of Steps ST11 to ST15. In a case where the error E2 is less than the predetermined threshold value Th2 in Step ST12, the repeated calculation processing ends.

Returning to FIG. 20, in a case where the repeated calculation processing ends, the second image generation section 106 outputs a processed radiation image Gm that has a primary radiation distribution Ipm derived on the basis of a body thickness distribution tm of the subject Obj where the error E2 is less than the predetermined threshold value Th2 as pixel values (Step ST7). The output processed radiation image Gm is displayed on the display 31 (Step ST8).

As described above, in the second embodiment, the body thickness distribution of the subject Obj is derived on the radiation image G0 and the imaging conditions and the primary radiation distribution Ip1 and the scattered radiation distribution Is1 of radiation, which is detected by the radiography panel 14, are derived using the imaging conditions, the body thickness distribution t, and the radiation characteristics of an element. Then, the error E2 between the sum Iw1 of the primary radiation distribution Ip1 and the scattered radiation distribution Is1 and a pixel value at each position in the radiation image G0 is derived, the body thickness distribution is updated so that the error E2 is less than the predetermined threshold value Th2, and the acquisition of the radiation characteristics and the derivation of the primary radiation distribution and the scattered radiation distribution based on the updated body thickness distribution are repeated. Accordingly, the primary radiation distribution Ip1 and the scattered radiation distribution Is1 can be derived in consideration of the radiation characteristics of an element interposed between the subject Obj and the radiography panel 14. Since the primary radiation distribution Ip1 derived in this way is a distribution obtained in consideration of the radiation characteristics of an element interposed between the subject Obj and the radiography panel 14, scattered radiation components have been accurately removed from the primary radiation distribution Ip1. Therefore, according to the second embodiment, a processed radiation image from which scattered radiation components are accurately removed can be acquired in consideration of an element interposed between the subject Obj and the radiography panel 14.

Figure 22:
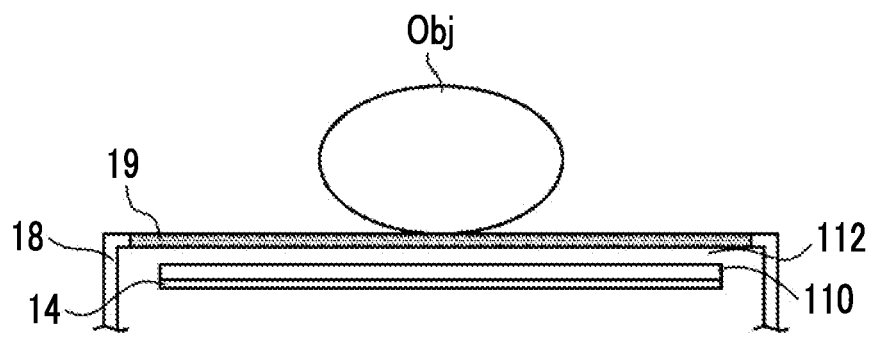
FIG. 22 is a diagram illustrating an air layer that is interposed between a top board and a grid.

In the second embodiment, the top board 19 of the imaging table 18 and the grid are used as an element interposed between the subject Obj and the radiography panel 14. However, as shown in FIG. 22, an air layer 112 may be interposed between the top board 19 and the grid 110. In such a case, it is preferable that the radiation distribution derivation unit 105 derives the primary radiation distribution Ip1 and the scattered radiation distribution Is1 in a state where the air layer 112 is also included in the element interposed between the subject Obj and the radiography panel 14. In this case, the convolution of a point spread function PSFair(kV(,mmAl),tair) corresponding to the thickness tair of the air layer 112 is performed on Equations (X6) and (X7), so that the primary radiation distribution Ip1 and the scattered radiation distribution Is1 may be derived as shown in Equations (X6-1) and (X7-1) to be described below. The thickness tair of the air layer 112 is a distance between the lower surface of the top board 19 and the surface of the grid 110 facing the subject Obj.

$$Ip1 = Ip0 \times Tp(kV(, mmA1), t) * PSFair(kV(, mmA1), tair) \quad (X6\text{-}1)$$

$$Is1 = Is0 \times Ts(kV(, mmA1), t) * PSFair(kV(, mmA1), tair) \quad (X7\text{-}1)$$

In the embodiments and the like, the hardware structures of processing units, which perform various types of processing, such as the first estimation section 36, the second estimation section 37, the first image generation section 38, the calculation unit 40, the imaging condition acquisition unit 102, the body thickness derivation unit 103, the characteristic acquisition unit 104, the radiation distribution derivation unit 105, and the second image generation section 106, are various processors to be described later. Various processors include: a central processing unit (CPU) that is a general-purpose processor functioning as various processing units by executing software (programs); a graphical processing unit (GPU); a programmable logic device (PLD) that is a processor of which the circuit configuration can be changed after manufacture, such as a field programmable gate array (FPGA); a dedicated electrical circuit that is a processor having circuit configuration designed exclusively to perform various types of processing; and the like.

One processing unit may be formed of one of these various processors, or may be formed of a combination of two or more same kind or different kinds of processors (for example, a combination of a plurality of FPGAs, a combination of a CPU and an FPGA, a combination of a CPU and a GPU, or the like). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor implementing the functions of the entire system, which includes a plurality of processing units, by one integrated circuit (IC) chip is used as typified by System On Chip (SoC) or the like. In this way, various processing units are formed using one or more of the above-mentioned various processors as hardware structures.

In addition, the hardware structures of these various processors are more specifically electrical circuitry where circuit elements, such as semiconductor elements, are combined.

EXPLANATION OF REFERENCES

10: radiography system
13: radiation source
14: radiography panel
15: first radiation detector
16: second radiation detector
17: radiation energy conversion filter
18: imaging table
19: top board
20: console
21: display
22: operation unit
30: radiation image processing device
31: display
32: operation unit
33: radiation image acquisition unit
34: storage
35: image processing unit
36: first estimation section
37: second estimation section
38: first image generation section
40: calculation unit
51: first radiation image
91: distribution
92: distribution
100: radiation image processing device
102: imaging condition acquisition unit
103: body thickness derivation unit
104: characteristic acquisition unit
105: radiation distribution derivation unit
106: second image generation section
110: grid
112: air layer
140: lead plate
141: phantom

What is claimed is:

1. A radiation image processing device comprising:
a processor configured to:
acquire a first radiation image that is taken from a subject by detecting radiation transmitted through the subject by a radiation detector in a state where an element is interposed between the subject and the radiation detector;
estimate a component of the radiation at a position between the subject and the element, which has passed through the subject, using the first radiation image;
estimate a component of the radiation, which has passed through the element through which the radiation further passes after passing through the subject, using an estimation result of the component of the radiation transmitted through the subject and scattering characteristics of the element; and
generate a second radiation image, in which an image of the subject is formed by the radiation transmitted through the subject and the element, using an estimation result of the component of the radiation transmitted through the element.

2. The radiation image processing device according to claim 1,
wherein the processor is further configured to estimate the component of the radiation transmitted through the subject and a component of the radiation scattered by the subject.

3. The radiation image processing device according to claim 1,
wherein the processor is further configured to estimate a body thickness of the subject using the first radiation image and estimates a component of the radiation having passed through the subject using the estimated body thickness of the subject.

4. The radiation image processing device according to claim 3,
wherein the processor is further configured to estimate the component of the radiation transmitted through the subject and a component of the radiation scattered by the subject on the basis of the estimated body thickness of the subject.

5. The radiation image processing device according to claim 1,
wherein the estimation result of the component of the radiation transmitted through the subject is an intensity distribution of the radiation having passed through the subject, and
the intensity distribution of the radiation having passed through the subject includes the component of the radiation transmitted through the subject and a component of the radiation scattered by the subject.

6. The radiation image processing device according to claim 1,
wherein the processor is further configured to estimate the component of the radiation transmitted through the subject and the element or a component of the radiation scattered by at least one of the subject or the element.

7. The radiation image processing device according to claim 6,
wherein the processor is further configured to estimate a component of the radiation, which has passed through the element, by causing the scattering characteristics of the element to act on the estimation result of the component of the radiation transmitted through the subject.

8. The radiation image processing device according to claim 1,
wherein the scattering characteristics determine a distribution of an amount of radiation to be transmitted through the element and/or an amount of radiation to be scattered by the element.

9. The radiation image processing device according to claim 8,
wherein the scattering characteristics include a first characteristic that determines the distribution of the amount of radiation to be transmitted through the element and a second characteristic that determines the distribution of the amount of radiation to be scattered by the element.

10. The radiation image processing device according to claim 1,
wherein the processor is further configured to generate the second radiation image by making an image of the estimation result of the component of the radiation transmitted through the element, in a case where the processor estimates the component of the radiation transmitted through the subject and the element.

11. The radiation image processing device according to claim 1,
wherein the processor is further configured to generate the second radiation image by subtracting the estimation result of the component of the radiation, which has been transmitted through the element, from the first radiation image, in a case where the processor estimates a component of the radiation scattered by the subject or the element.

12. The radiation image processing device according to claim 1,
wherein the processor is further configured to
detect the radiation transmitted through the subject by a radiation detector in a state where the element is interposed between the subject and the radiation detector and acquire an imaging condition at a time of acquisition of a radiation image of the subject,
derive a body thickness distribution of the subject on the basis of the radiation image and the imaging condition,
acquire radiation characteristics of the element corresponding to the body thickness distribution,
derive a primary radiation distribution and a scattered radiation distribution of the radiation, which is detected by the radiation detector, using the imaging condition, the body thickness distribution, and the radiation characteristics of the element, and
calculate an error between a sum of the primary radiation distribution and the scattered radiation distribution and a pixel value at each position in the radiation image, update the body thickness distribution so that the error is less than a predetermined threshold value, and repeat the derivation of the radiation characteristics and the derivation of the primary radiation distribution and the scattered radiation distribution based on the updated body thickness distribution.

13. The radiation image processing device according to claim 12,
wherein the processor is further configured to output a processed radiation image that has the primary radiation distribution derived on the basis of the body thickness distribution of the subject where the error is less than the threshold value as pixel values.

14. The radiation image processing device according to claim 12,
wherein a first table that shows a relationship between the body thickness distribution and scattered radiation transmittance of the element interposed between the subject and the radiation detector, or a second table that shows a relationship between the body thickness distribution and primary radiation transmittance of the element interposed between the subject and the radiation detector is stored in a storage, and
the processor is further configured to acquire the primary radiation transmittance or the scattered radiation transmittance, which is radiation characteristics of the element corresponding to the body thickness distribution, with reference to the first and second tables according to the imaging condition.

15. The radiation image processing device according to claim 12,
wherein the element is at least one of an imaging table on which the subject is to be placed, a top board, a grid, or an air layer.

16. A radiation image processing method executed by a processor, the method comprising:
a step of acquiring a first radiation image that is taken from a subject by detecting radiation transmitted through the subject by a radiation detector in a state where an element is interposed between the subject and the radiation detector;
a step of estimating a component of the radiation at a position between the subject and the element, which has passed through the subject, using the first radiation image;
a step of estimating a component of the radiation, which has passed through an-the element through which the radiation further passes after passing through the subject, using an estimation result of the component of the radiation having passed through the subject and scattering characteristics of the element; and
a step of generating a second radiation image, in which an image of the subject is formed by the radiation transmitted through the subject and the element, using an estimation result of the component of the radiation having passed through the element.

17. The radiation image processing method executed by a processor according to claim 16, further comprising:
a step of detecting the radiation transmitted through the subject by a radiation detector in a state where the element is interposed between the subject and the radiation detector and acquiring an imaging condition at a time of acquisition of a radiation image of the subject;

a step of deriving a body thickness distribution of the subject on the basis of the radiation image and the imaging condition;

a step of acquiring radiation characteristics of the element corresponding to the body thickness distribution;

a step of deriving a primary radiation distribution and a scattered radiation distribution of the radiation, which is detected by the radiation detector, using the imaging condition, the body thickness distribution, and the radiation characteristics of the element; and a step of calculating an error between a sum of the primary radiation distribution and the scattered radiation distribution and a pixel value at each position in the radiation image, updating the body thickness distribution so that the error is less than a predetermined threshold value, and repeating the derivation of the radiation characteristics and the derivation of the primary radiation distribution and the scattered radiation distribution based on the updated body thickness distribution.

18. A radiation image processing method executed by a processor, the method comprising:

a step of detecting radiation transmitted through a subject by a radiation detector in a state where an element is interposed between the subject and the radiation detector and acquiring an imaging condition at a time of acquisition of a radiation image of the subject;

a step of deriving a body thickness distribution of the subject on the basis of the radiation image and the imaging condition;

a step of acquiring radiation characteristics of the element corresponding to the body thickness distribution;

a step of deriving a primary radiation distribution and a scattered radiation distribution of the radiation, which is detected by the radiation detector, using the imaging condition, the body thickness distribution, and the radiation characteristics of the element; and a step of calculating an error between a sum of the primary radiation distribution and the scattered radiation distribution and a pixel value at each position in the radiation image, updating the body thickness distribution so that the error is less than a predetermined threshold value, and repeating the derivation of the radiation characteristics and the derivation of the primary radiation distribution and the scattered radiation distribution based on the updated body thickness distribution.

\* \* \* \* \*